(12) United States Patent
Wilson et al.

(10) Patent No.: US 10,751,720 B2
(45) Date of Patent: Aug. 25, 2020

(54) BIOCHIP WELL, SEALED WELL ASSEMBLY, CARTRIDGE THEREFOR, AND APPARATUS AND METHODS FOR OPENING SEALED WELLS

(71) Applicants: Gareth Wilson, Waringstown (GB); Michael Hooks, Loughall (GB); Peter Fitzgerald, Crumlin (GB); John Lamont, Crumlin (GB); Ivan McConnell, Crumlin (GB)

(72) Inventors: Gareth Wilson, Waringstown (GB); Michael Hooks, Loughall (GB); Peter Fitzgerald, Crumlin (GB); John Lamont, Crumlin (GB); Ivan McConnell, Crumlin (GB)

(73) Assignee: RANDOX LABORATORIES LTD., Crumlin (GB)

( * ) Notice: Subject to any disclaimer, the term of this patent is extended or adjusted under 35 U.S.C. 154(b) by 633 days.

(21) Appl. No.: 15/360,038

(22) Filed: Nov. 23, 2016

(65) Prior Publication Data

US 2017/0095819 A1 Apr. 6, 2017

Related U.S. Application Data

(62) Division of application No. 13/812,767, filed as application No. PCT/GB2011/051427 on Jul. 26, 2011, now Pat. No. 9,540,129.

(30) Foreign Application Priority Data

Jul. 26, 2010 (GB) .................................. 1012490.7

(51) Int. Cl.
*B01L 9/00* (2006.01)
*B01L 3/00* (2006.01)
(Continued)

(52) U.S. Cl.
CPC .............. *B01L 9/52* (2013.01); *B01L 3/5085* (2013.01); *B01L 9/527* (2013.01); *B65B 69/00* (2013.01);
(Continued)

(58) Field of Classification Search
CPC .......... B01L 9/52; B01L 3/5085; B01L 9/527; B65B 69/00; B65D 71/50; G01N 1/28; G01N 33/50
See application file for complete search history.

(56) References Cited

U.S. PATENT DOCUMENTS

| | | |
|---|---|---|
| 5,277,874 A | 1/1994 | Vasta |
| 5,282,543 A | 2/1994 | Picozza et al. |

(Continued)

FOREIGN PATENT DOCUMENTS

| | | |
|---|---|---|
| DE | 20 2009 002 026 U1 | 6/2009 |
| EP | 1 374 989 A2 | 1/2004 |

(Continued)

OTHER PUBLICATIONS

Nov. 29, 2011 International Search Report issued in Application No. PCT/GB2011/051427.

(Continued)

*Primary Examiner* — Sally A Merkling
(74) *Attorney, Agent, or Firm* — Oliff PLC

(57) ABSTRACT

A biochip well is disclosed, including a vessel containing a well therewithin, the vessel forming at least base and side walls of the well and defining at least one aperture giving access to the well, and further including retaining means for holding a biochip at a predetermined position within the well, the well including a laterally offset region into which the biochip does not protrude when held at the predeter- (Continued)

mined position by the retaining means. Also disclosed are sealed well assemblies and apparatus and methods for opening sealed wells.

19 Claims, 15 Drawing Sheets

(51) Int. Cl.
    *B65B 69/00*     (2006.01)
    *G01N 1/28*     (2006.01)
    *G01N 33/50*     (2006.01)
    *B65D 71/50*     (2006.01)

(52) U.S. Cl.
CPC ............... *B65D 71/50* (2013.01); *G01N 1/28* (2013.01); *G01N 33/50* (2013.01); *B01L 2200/025* (2013.01); *B01L 2300/044* (2013.01); *B01L 2300/0609* (2013.01); *B01L 2300/0636* (2013.01); *B01L 2300/0819* (2013.01); *B01L 2300/0822* (2013.01); *Y10T 436/2575* (2015.01)

(56) References Cited

U.S. PATENT DOCUMENTS

| | | | |
|---|---|---|---|
| 7,159,740 B2* | 1/2007 | Nanthakumar | B01L 9/56 221/224 |
| 2003/0049865 A1 | 3/2003 | Santini et al. | |
| 2003/0124735 A1 | 7/2003 | Nanthakumar et al. | |
| 2003/0217945 A1 | 11/2003 | Kiene et al. | |
| 2004/0101966 A1 | 5/2004 | Davis et al. | |
| 2005/0226779 A1* | 10/2005 | Oldham | B01L 3/5025 422/400 |
| 2005/0232822 A1 | 10/2005 | Reed et al. | |
| 2005/0274395 A1 | 12/2005 | Haga | |
| 2005/0282156 A1 | 12/2005 | Rava et al. | |
| 2006/0180489 A1 | 8/2006 | Guiney et al. | |
| 2007/0172393 A1 | 7/2007 | Beer | |
| 2008/0072994 A1 | 3/2008 | Kim et al. | |
| 2009/0221092 A1 | 9/2009 | Fujita | |

FOREIGN PATENT DOCUMENTS

| | | |
|---|---|---|
| WO | 2004/001389 A1 | 12/2003 |
| WO | 2006085604 A1 | 8/2006 |
| WO | 2009/103416 A1 | 8/2009 |

OTHER PUBLICATIONS

Oct. 26, 2012 International Preliminary Report on Patentability issued in Application No. PCT/GB2011/051427.
Aug. 8, 2012 Written Opinion of the International Preliminary Examining Authority issued in Application No. PCT/GB2011/051427.
Nov. 29, 2011 Written Opinion of the International Searching Authority issued in Application No. PCT/GB2011/051427.
Feb. 6, 2020 Office Action issued in European Patent Application No. 11 743 592.5.

* cited by examiner

BIOCHIP WELL, SEALED WELL ASSEMBLY, CARTRIDGE THEREFOR, AND APPARATUS AND METHODS FOR OPENING SEALED WELLS

This is a Divisional of application Ser. No. 13/812,767 filed May 7, 2013, which in turn is a 371 of International Patent Application No. PCT/GB2011/051427, filed Jul. 26, 2011. The disclosures of the prior applications are hereby incorporated by reference herein in their entirety. This invention relates to sealed wells for the storage of biochips or other components required to be kept sealed from the environment, as well as apparatus and methods for opening the sealed wells.

BACKGROUND

Biochips are components used for example in chemical analysis (including Proteomic and Molecular analysis) either to host a test reaction and/or to supply samples under test or reagents. Generally, a Biochip comprises a solid substrate on which is arranged one or more test sites at which a reaction can take place in use. For instance, the test site may carry one or more reagents (e.g. ligands such as antibodies or antigens) adsorbed to the substrate, which are activated by the addition of a sample substance (e.g. analytes present in the sample bind to specific ligands). Such chips are sometimes referred to as a "lab on a chip" and can also incorporate tools for controlling steps of a reaction. As an example, one Biochip supplied by Randox Laboratories Ltd is used as a medium for performing multiplex analysis of biological samples using a chemiluminescence method. In this example, the Biochip takes the form of a small ceramic chip with a specialized surface preparation which is sensitive to environmental degradation. Therefore the Biochip is generally delivered in an environmentally sealed format, usually evacuated, sealed foil bags.

For instance, the Evidence™ analyzer by Randox Laboratories Ltd uses biochips which are fitted into a plastic holder defining three recesses arranged in a line. Each recess is approximately square and sized to just accommodate a biochip, which is also square, with a small clearance to allow the chip to be placed. The "strip" of three mounted biochips are placed within a sealed foil bag for storage, which is then opened when the biochips are required for use. The plastic holder may be placed on a carrier alongside two further strips of three biochips to form a 3×3 array of biochips. The carrier has a keying feature for engagement with a robotic arm such that the array can be transported within the analyzer via robotic handling. This configuration is useful for batch analysis but not suitable for randomized work loads.

In some types of analyzing apparatus for performing chemical or biological tests, individual chips must be available to be used in any order required by the lab's workload. Therefore individual chips could remain unused onboard the system for days or weeks and are required to remain viable. Further, it can be necessary to supply the apparatus with more than one of each chip type.

Therefore a means of sealing and automatically opening the individual chips at time of use is required.

In some known analyzing apparatus, such as the Evidence™ analyzer mentioned above, biochips are carried in a tray with individual recesses for each biochip. During analysis, reagents and/or samples are dispensed on to the chip within the recess, e.g. by pipetting. This can give rise to "trending" in the results: for instance, reaction sites closest to the position at which the reagent or sample is dropped onto the chip may be exposed to a higher concentration of the reagent or sample than sites further away, due to intermediate sites having bound active components of the reagent or sample as the fluid spreads across the surface of the chip. The test results could therefore be artificially skewed and typically this may be addressed by consistently dispensing the reagent or sample at precisely the same location on the chip, so that the trending may be predicted and compensated for when analyzing the results. A very high degree of control of the reagent and sample dispensing probes is therefore desired.

In addition, at various steps during the analysis, the recess may need to be evacuated (of air, water or other fluid, e.g. sample or reagents) and this is typically performed using a vacuum probe inserted into the recess holding the chip. The vacuum probe movement must be also controlled to a high degree of accuracy in order to avoid contact with the biochip surface itself, which could contaminate the chip and/or damage the test site(s) on its surface.

SUMMARY

A first aspect of the present invention provides a biochip well comprising a vessel containing a well therewithin, the vessel forming at least base and side walls of the well and defining at least one aperture giving access to the well, and further comprising retaining means for holding a biochip at a predetermined position within the well, the well including a laterally offset region into which the biochip does not protrude when held at the predetermined position by the retaining means.

Thus, the well includes a region into which the biochip does not extend once it is fitted into the well using the retaining means provided. This allows for dispensing and/or evacuation of fluids to or from the well to take place away from the chip itself. For example, when dispensing reagent or sample, the dispensing probe can be inserted above the laterally offset region and the fluid dispensed "off-chip" (i.e. not directly onto the chip's surface). The fluid collects in the base of the well which is gradually filled until the chip is submerged by the fluid. This achieves far more even fluid coverage of the biochip surface, with the result that the test sites on the chip each received reagent or sample of approximately equal concentration, and the effects of trending are substantially reduced. Further, the dispensing and/or vacuum probes can be inserted into the well at a position which is spaced from the chip in use, thereby reducing the risk of collision between the probe and the biochip. As a whole, the need for highly precise positional control of the probes is reduced and, in consequence, if desired, the probe movement can be accelerated, enabling a faster step completion time and ultimately contributing to high throughput speeds of the analyzing apparatus used to carry out the tests.

Preferably, the laterally offset region is offset in the plane defined by the surface of the biochip when held at the predetermined position by the retaining means. Typically, the biochip will sit approximately parallel to the base wall of the well, and hence the laterally offset region preferably includes a portion of the base wall which is not covered by the biochip in use. The aperture giving access to the well is typically in the upper surface of the vessel (opposite the base wall), and hence configuring the well in this way allows for a probe to be inserted vertically through the aperture directly over the laterally offset region (rather than the chip). The laterally offset region is preferably open and uncovered for receipt of the fluid/probe.

The laterally offset region could take any size and/or shape, since the biochip is fixed in a location outside the region by the retaining means in use. However, in preferred embodiments, the shape and/or size of the laterally offset region is such that the biochip cannot be accommodated therewithin. This assists in the loading of the biochip into the well since the biochip cannot inadvertently be placed in the laterally offset region. Further, this arrangement keeps the size of the well to a minimum. That said, if the laterally offset region is too small, it may be difficult to dispense fluid into the region without the fluid first contacting the biochip and also to insert a probe into the region without contacting the biochip. Therefore the region preferably has a surface area (in the same plane as the biochip) of at least 20 $mm^2$, more preferably at least 25 $mm^2$, still preferably at least 30 $mm^2$. It is also preferred that the region is not overly elongate (i.e. much narrower in one direction than the other) since this would also give rise to a need for high positional accuracy of the probe. A minimum preferred width of the region is 4 mm, more preferably 5 mm, and a minimum preferred length of the region is 4 mm, more preferably 5 mm. In preferred embodiments, the region 7 at least encompasses a square or rectangular area of around 4 mm by 4 mm, 4 mm by 5 mm or 5 mm by 5 mm, or a substantially circular area of around 4 to 5 mm diameter. Of course, the region may well be larger than this (i.e. encompassing additional 'areas' alongside the square/circle/rectangle) in practice.

More than one laterally offset region may be provided, but in this case at least one of the regions should be sufficiently large to encompass the dimensions and/or areas mentioned above. Due to the presence of the laterally offset region(s), the overall area of the well typically has a different shape from that of the biochip itself, although this is not essential if the well is sufficiently large compared to the biochip.

In particularly preferred embodiments, the laterally offset region has a width which decreases with increasing distance from the predetermined position in which the biochip is held. For instance, the maximum width of the region may be approximately equal to that of the chip, the subsequently decreasing width preventing entry of the chip into the region. Such arrangements allow for good fluid flow between the area of the well holding the chip and the region where the probe will be inserted. Preferably, the laterally offset region has a cross section in the lateral plane which is triangular, curved, semi-circular or semi-elliptical.

The retaining means could comprise any mechanism or substance capable of fixing the position of the chip within the well. Preferably, the retaining means constrain the chip laterally (i.e. sideways) as well as vertically (i.e. in and out of the well). In preferred embodiments, the retaining means comprise one or more interference fit features provided on the side and/or base walls of the well, adapted to grip the biochip in use. For instance, the interference fit features could comprise one or more protrusions extending towards the interior of the well from one or more of the walls, which together define a smaller volume which exactly accommodates the chip such that friction between the feature(s) and the chip prevent its easy removal. Alternatively, the retaining means could comprise for example an adhesive, a mechanical clip, ultrasonically formed protrusions from the side wall(s), mechanical punctures through the side wall(s), mechanically formed protrusions from the side walls, a snap-in insert or collar.

In an especially preferred embodiment, the retaining means comprises at least one protrusion extending from an internal wall of the well, the at least one protrusion being deformable such that in use the at least one protrusion can be mechanically deformed to extend over a portion of the biochip, when the biochip is at the predetermined position. The or each protrusion can form part of the aforementioned interference fit feature(s) and so perform the dual functions of gripping the biochip around its periphery and also physically obstructing its removal by extending over the top of the chip by a small distance. A particularly preferred technique for fitting the biochip using such a protrusion is given below.

Preferably, the biochip well further comprises a keying feature for engagement with a transport mechanism, such as a robotic arm. This may for example take the form of a shaped protrusion or tab integral with the vessel, which is designed to mate with or be clamped by a component of the transport mechanism. In this way, each individual biochip well can be transported within the analyzer without need for conveying as part of a batch. As such, the biochips can be used in any order upon demand, according to the analyzer's work load. Further, there is no need for any additional carrier component for engagement with the transport mechanism, whereby the part count is reduced, and the number of steps required for automatic production is also reduced and simplified.

The first aspect of the invention also provides a biochip well assembly comprising a biochip well as described above and a biochip mounted in the predetermined position by the retaining means.

Also provided is a method of manufacturing a biochip well assembly, comprising:
(i) providing a vessel containing a well therewithin, the vessel forming at least base and side walls of the well and defining at least one aperture giving access to the well and retaining means for holding a biochip at a predetermined position within the well, the retaining means comprising at least one protrusion extending from an internal wall of the well;
(ii) placing a biochip in the predetermined position; and
(iii) deforming the at least one protrusion such that at least part of the at least one protrusion extends over a portion of the biochip to retain the biochip at the predetermined position.

This technique has been found by the present inventors to achieve a particularly effective retention of the biochip inside the well, since the deformed protrusion physically obstructs the passage of the biochip out of the predetermined position. Further by deforming a specifically designed protrusion, rather than a section of the vessel wall itself, the extent of the obstruction is precisely controlled, such that overlap with any of the test sites can be avoided. In addition, the pre-existing protrusions typically contact the sides of the biochip and therefore also constrain the biochip laterally. The deformation could be achieved in a number of ways such as heating the protrusion or applying ultrasonic vibration. However, preferably step (iii) comprises applying pressure to the at least one protrusion to mechanically deform the protrusion. This avoids heating the biochip (which in many cases need to be stored at specific temperatures in order to preserve substances carried at the test sites) and also enhances control of the overlap.

This approach can be contrasted with conventional techniques which include (in the case of the Evidence™ biochips, for example) placing the biochip in the square based recess using a vacuum head and then pushing in a set of ultrasonic horns from each side wall to form dimple protrusions which hold the chip in place. Here, the side wall itself is deformed to form each protrusion. This has been found to allow the chip a small amount of movement relative to the recess during operation. Further, the ultrasonic forming stage has also been known to break chips if the chip is incorrectly placed in the recess prior to staking. Finally, if the dimples are created to high up the walls relative to the chip, the chip can fall out of the recess in transit. The presently disclosed technique, in contrast, increases the positional accuracy of the biochip and also avoids such manufacturing problems.

The biochip could be placed in the well using various different techniques such as (automated or manual) tweezers or other form of mechanical gripping, but preferably step (ii) comprises using a vacuum tool to hold and then deposit the biochip at the predetermined position. That is, the biochip is held against the head of the tool through the application of low air pressure, and then deposited into the well by release of the vacuum. This enables a particularly advantageous implementation of the method whereby step (iii) comprises using the head of the vacuum tool to apply pressure to the at least one protrusion. The tool head may be equipped with a shaped platform for this purpose. This keeps the number of parts required for assembly down, and speeds up the assembly process.

In particularly preferred embodiments, the at least one protrusion forms at least part of an interference fit feature adapted to grip the biochip in use. For instance, the protrusion may take the form of an elongate rib extending up the side wall of the well. To achieve the interference fit, the depth of the rib may increase towards the base wall of the well, such that when lowered into the predetermined position, the rib gradually meets the side of the chip. The chip becomes wedged between the rib and another feature (which could be another similar rib or the side wall of the well). A portion of the rib immediately above the so-positioned chip may then be deformed as described above to fully retain the chip in place.

The well itself could take any convenient form but in preferred embodiments includes a laterally offset region into which the biochip does not protrude when held at the predetermined position by the retaining means, in the same manner as already described.

The invention also provides a method of carrying out a test reaction using a biochip well assembly as already described, comprising:
 (I) providing a biochip well assembly in accordance with the first aspect of the invention;
 (II) dispensing fluid into the well at an off-chip position within the laterally offset region; and
 (III) continuing to dispense fluid at the off-chip position until the biochip is submerged in the fluid.

As described above, by dispensing fluid at an off-chip position such that it is not dispensed directly onto the chip surface, but rather rises up to cover the chip from the base of the well, trending is avoided. This provides the significant benefit that highly precise positional control of the dispensing probe is no longer required, and the speed of dispensation can be increased. Any fluid could be handled in this manner but preferably, the fluid comprises a reagent, a sample or a diluent.

Preferably, the method further comprises:
 (IV) removing at least some of the fluid from the well by inserting a vacuum probe into the fluid at an off-chip position within the laterally offset region and extracting fluid through the probe.

In a second aspect, the present invention provides a sealed well assembly for the storage of biochips, comprising one or more vessels affixed to a sealing sheet, the or each vessel having at least one well defined therein for containing a biochip, the or each well being sealed by the sealing sheet, the or each well preferably containing a biochip.

Forming a sealed package for the or each biochip in this way enables each individual chips to be kept hermetically sealed until it is required for a test. As will be described below, the construction allows for automatic, machine controlled release of each chip from the sealed well assembly by an analyzing apparatus as and when it is needed.

Preferably, the sealed well assembly comprises a plurality of wells. Several wells could be provided in a single vessel, but preferably, the assembly comprises a plurality of vessels, each defining a well, e.g. a single well. The plurality of vessels are preferably individual, i.e. not connected to one another other than by the sealing sheet. Typically the vessels will be spaced from one another on the sealing sheet by a small distance although this is not essential.

In preferred examples, the plurality of wells and/or the plurality of vessels are arranged along a rectilinear line on the sealing sheet. The sealing sheet may be a strip or belt.

The sealing sheet preferably extends beyond the perimeter of the vessel(s) in at least one direction. In particularly preferred cases, where there are multiple wells arranged in a straight line (in one or more vessels), the sealing sheet extends beyond the vessel(s) in the same direction as defined by the line of wells. This extension of the sealing sheet makes the assembly particularly well adapted for use in an apparatus for opening the sealed wells such as that described below. For instance, the extended region(s) ahead of or following the wells may be wound onto a spool or otherwise gripped by components of the apparatus. In preferred examples, the or each extended region of the sheet (i.e. those regions not carrying vessels) is at least as long as one of the wells in the same direction. For instance, the or each extended region may be at least 1.5 cm long, preferably at least 2 cm long, more preferably at least 5 cm long.

In particularly preferred implementations, the length of the sheet extending beyond the vessel(s) is at least as long as the portion of the sheet to which the vessel(s) are attached (both lengths being measured in the direction parallel to the line of wells). This may be a combined length taking into account regions of the sheet extending both in front of or behind the line of wells. This enables the two ends of the sheet to be joined directly to one another around a guide plate, forming a closed loop. However, the same effect can be achieved with shorter extension regions if a clip or other component is provided to hold the two ends in fixed relation, the clip extending between one and the other. This will be described further below.

Advantageously, the vessel(s) are affixed to the sealing sheet by heat sealing, an adhesive or ultra sonic welding. The sealing sheet could be made of any material suitable for sealing the well and maintaining the necessary environment, but in preferred examples it may comprise a metal foil, a polymer sheet, polymer layer, or cellulose-based material, or any combination thereof, and is preferably of multilaminate construction. For example, the sheet could comprise an aluminium strip, or an aluminium foil and polymer laminate. The material may be coated, e.g. to improve sealing and/or to protect against corrosion. Suitable coating materials include polypropylene, polyethylene and polystyrene.

In particularly preferred embodiments, the or each well of the sealed well assembly is a biochip well in accordance with the first aspect of the invention, described above.

In a third aspect, the present invention provides a cartridge for a sealed well assembly as defined above, configured to accommodate the vessel(s). The cartridge can help to protect the vessels and also assists in handling and loading.

Preferably the cartridge comprises a guide structure adapted to constrain movement of the vessel(s) within the cartridge along a vessel path, and to receive the sealing sheet and define a sheet path along which the sealing sheet can travel. In preferred examples, the guide structure comprises a guide plate against which a region of the sealing sheet to which the vessel(s) are attached is placed in use, preferably a substantially flat guide plate. Advantageously, the guide structure has a square, rectangular or substantially "D" or "U"-shaped cross section, one floor of which is defined by the guide plate, for accommodating the vessel(s) therewithin.

In particularly preferred embodiments, the guide structure further comprises a guide channel adjacent an end of the cartridge, the guide channel being adapted to cooperate with the or each vessel so as to prevent rotation thereof. For example, the guide structure may comprise an elongate keying feature (such as a recess or protrusion on one or more of the (internal) walls of the cartridge), adapted to slidably engage with a corresponding feature on the or each vessel.

In certain preferred embodiments, the cartridge may comprise a drive member for transferring drive to the sealed well assembly, preferably a driven spool on to which an end of the sealing strip is wound in use, or a driven pulley for conveying the sealing strip along its path. Typically the drive member will itself be driven by an external motor, forming part of an analyzer apparatus into which the cartridge is inserted, for example, but in other examples a motor could be incorporated into the cartridge and appropriate power and/or controller connections provided.

In accordance with a fourth aspect, the present invention also provides a cartridge assembly comprising a cartridge and a sealed well assembly, both as described above in connection with the second and third aspects of the invention. Preferably, the sealing sheet extends around the guide plate so as to form a closed loop. Advantageously, the two ends of the sealing sheet are joined, preferably by heat sealing, ultrasonic welding, mechanical crimping or with a clip or an adhesive.

In a fifth aspect of the invention, an apparatus is provided for opening a sealed well assembly as described above in connection with the third aspect, comprising a drive mechanism adapted to convey the sealed well assembly such that the sealing sheet travels along a sheet path and the vessel(s) follow a vessel path, wherein the sheet path and vessel path diverge from one another such that the vessel is released from the sealing sheet and the well is opened.

The sealing sheet thus acts as a belt to which the one or more vessels are attached. Driving the sheet or the vessels forward brings them to a point at which the sheet is forced to diverge from the vessel, thereby opening the well. The waste material (sealing sheet) is retained as a single piece, allowing for easy disposal, and the well containing the biochip is presented for onward processing and analysis. The number of wells opened can be accurately controlled through control of the drive mechanism.

Preferably, the apparatus is adapted to receive or comprises a cartridge or a cartridge assembly, both as defined above, such that the guide structure of the cartridge can be used to define the vessel path and/or the sheet path, at least in part.

The apparatus may be configured to dispense wells from a single sealed well assembly. However, in some cases it is highly desirable to have available multiple different types of biochip, and to select which type of biochip is dispensed according to the test(s) to be conducted. According to the present invention it is advantageous to provide each different biochip type in a different sealed well assembly.

To enable dispensing from multiple different sealed well assemblies, in a preferred embodiment, the apparatus further comprises a cartridge support structure adapted to receive a plurality of cartridges or cartridge assemblies, each as defined above, wherein the guide structure of each cartridge defines a respective vessel path and a respective sheet path, at least in part. The differently-loaded cartridges can be mounted onto the support and replaced as necessary.

Chips can be dispensed from the multiple cartridges using a number of alternative techniques. In a first preferred implementation, the drive mechanism is movable relative to the cartridge support structure such that in use the drive mechanism conveys a sealed well assembly in a selected one of the plurality of cartridges carried by the cartridge support structure. This allows for the provision of a single drive mechanism capable of actuating any of (or at least a subset of) the available cartridges, thereby simplifying construction and keeping the part count low.

In a second preferred implementation, a corresponding plurality of drive mechanisms are provided for conveying a sealed well assembly in each of the plurality of cartridges carried by the cartridge support structure in use. That is, a drive mechanism is provided for each of the available cartridge positions on the support. This can enable faster dispensation since there is no requirement to move the drive mechanism and/or cartridges prior to beginning dispensing.

In particularly preferred embodiments, the sealing sheet is configured as a closed loop and the drive means is adapted to drive the sealing sheet around the loop, the drive mechanism preferably comprising at least one driven wheel arranged to contact the sealing sheet or vessel(s). It should be noted that, to form the closed loop, the two ends of the sealing sheet need not directly contact one another (although this is preferred) since a clip or other component may be provided to hold the two ends and thereby complete the loop. In other examples the sealing sheet may follow an open path—e.g. the drive means may comprise a leading edge drive unit for conveying the sealing sheet along the sheet path and, preferably, a trailing edge idler unit for controlling the trailing end of the sealing sheet.

The drive mechanism can be configured in various ways such as the at least one driven wheel mentioned already, and may transfer motion to the vessel(s) rather than directly to the sealing sheet if preferred (which will also result in motion of the sealing sheet). In one example, the drive mechanism comprises a linear actuator arranged to engage a respective keying feature provided on the sealing sheet or vessel(s).

This aspect of the invention also provides an apparatus for opening a sealed well in a vessel, wherein the well is sealed by a sealing sheet affixed to the vessel, the apparatus comprising:

a guide structure configured to receive the vessel and to constrain movement of the vessel along a vessel path;

the guide structure being further configured to receive the sealing sheet and to define a sealing sheet path along which the sealing sheet can be driven; and a drive mechanism adapted to drive the sealing sheet along the sealing sheet path and/or to drive the vessel along the vessel path;

wherein a first section of the vessel path and of the sealing sheet path are parallel and, at a position downstream of the first section, the vessel path and the sealing sheet path diverge such that, in the first section, when the sheet is driven the vessel and sheet remain affixed to one another and, at the diverging position, the sheet is stripped off the vessel, thereby opening the well.

Thus, dispensation of the chips from the sealed well structure can be performed without the use of any cartridge component. Nonetheless, in preferred embodiments, the guide structure is provided, at least in part, in the form of a cartridge which is removable from and reinsertable into the apparatus.

The cartridge can be as defined above. Advantageously, the guide structure comprises a vessel guide and a sheet guide. Preferably, the sealed well contains a biochip.

As before, it may be desirable to dispense from multiple sealed well assemblies and therefore the apparatus preferably comprises a plurality of the said guide structures. Again, the plurality of guide structures may be dispensed using a single drive mechanism which is movable relative to the guide structures, or a plurality of dedicated drive mechanisms may be used.

The drive mechanism could be manually controlled but preferably the apparatus further comprises a controller adapted to control the drive mechanism to drive the sealing sheet for a certain time or distance such that a desired number of wells are opened. The controller may receive inputs from an analyzer of which the apparatus forms part.

Where the apparatus is adapted to dispense from multiple sealed well assemblies (or cartridges) using a single drive mechanism, the apparatus preferably further comprises a controller adapted to control relative movement between the drive mechanism and the plurality of guide structures.

The invention also provides an analyzer for performing chemical or biochemical tests comprising an apparatus as described in connection with the fourth aspect of the invention.

In a sixth aspect, the invention provides a method of opening a sealed well in a vessel, comprising:
(a) providing a sealed well assembly, comprising one or more vessels affixed to a sealing sheet, the or each vessel having at least one well defined therein, the or each well being sealed by the sealing sheet; and
(b) driving the sealed well assembly such that the sealing sheet follows a sealing sheet path and the vessel(s) follow a vessel path;
wherein the sealing sheet path and vessel path diverge from one another such that the vessel is released from the sealing sheet and the well is opened.

Preferably, the sealed well assembly is as described above. Advantageously, the sealing sheet path follows a closed loop. Alternatively, the sealing sheet path can follow an open path. In preferred examples, the vessel path is substantially rectilinear (at least where the paths diverge).

Preferably, the vessel path and sheet path are parallel to each other at least in a first region upstream of the point of divergence. Advantageously, the vessel path and sheet path are rectilinear in the first region.

Where it is desired to dispense biochips from multiple different sealed well assemblies, in step (a), a plurality of sealed well assemblies are provided, each as defined above, and the method further comprises, prior to step (b):
(a1) selecting one of the plurality of sealed well assemblies in which a vessel is to be opened; and
(a2) selecting a drive mechanism corresponding to the selected sealed well assembly; or
(a3) moving the plurality of sealed well assemblies relative to a drive mechanism.

In preferred implementations, the method uses an apparatus as described above in connection with the fourth aspect of the invention.

BRIEF DESCRIPTION OF THE DRAWINGS

Examples of biochip wells, sealed well assemblies, cartridges, cartridge assemblies and methods and apparatus for opening sealed wells will now be described with reference to the accompanying drawings, in which.

DETAILED DESCRIPTION OF EMBODIMENTS

Figure 1A:
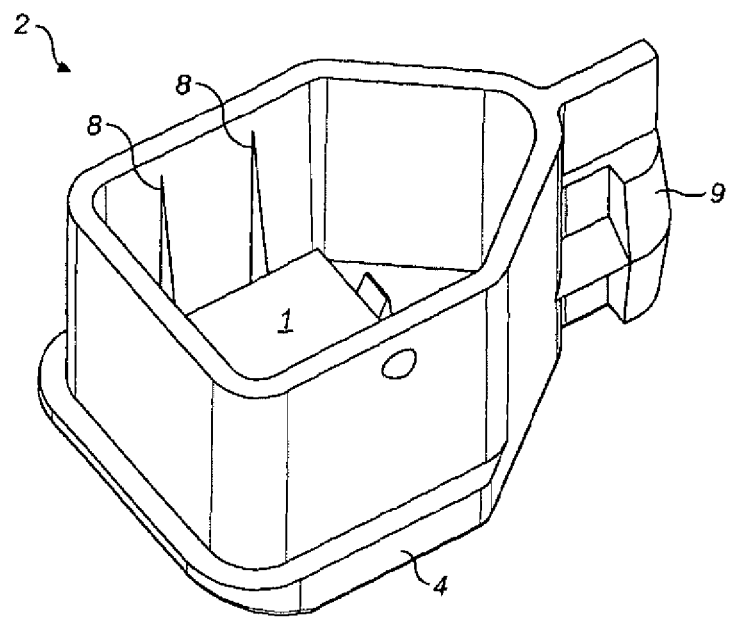
FIGS. 1(a), (b), (c) and (d) show an embodiment of a biochip well containing a biochip.
Figure 1B:
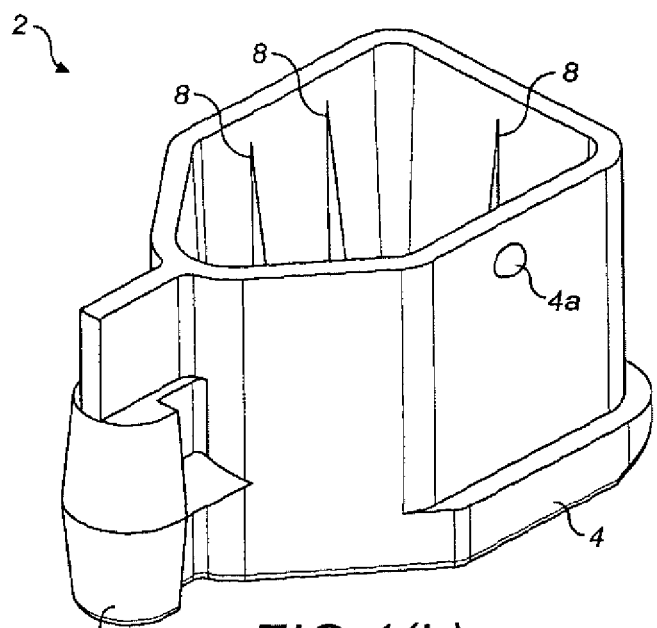
Figure 1C:
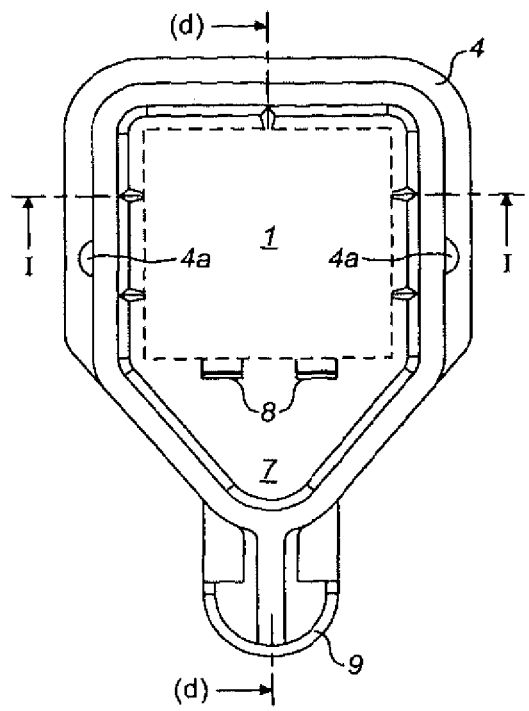
Figure 1D:
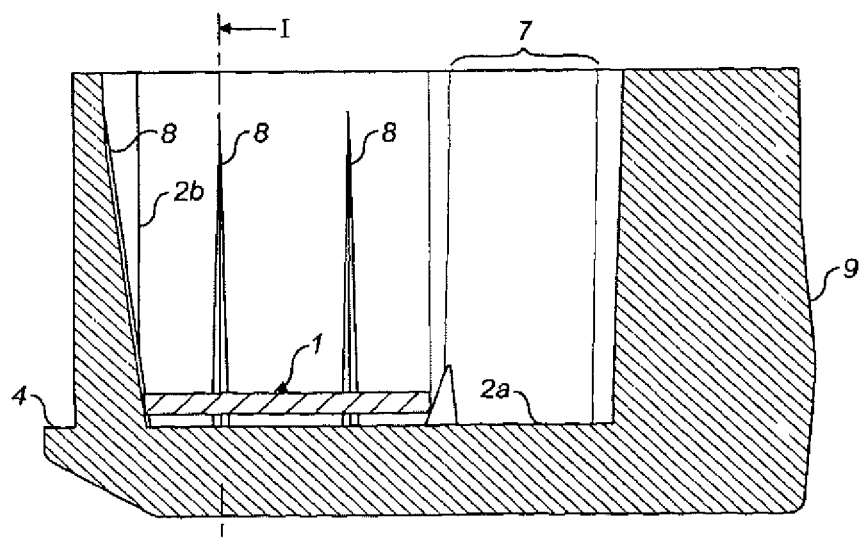
Figure 2A:
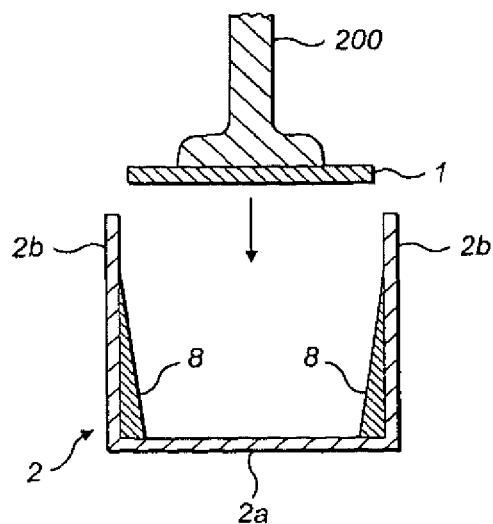
FIGS. 2(a) to (d) depict steps of an embodiment of a method of manufacturing a biochip well assembly.
Figure 2B:
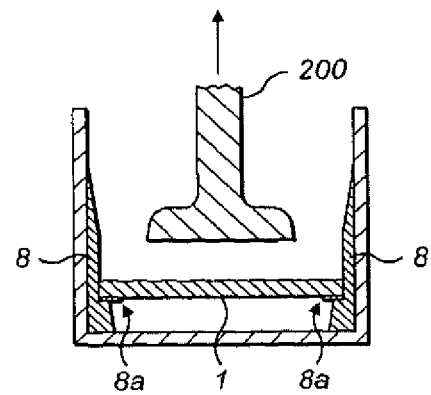
Figure 2C:
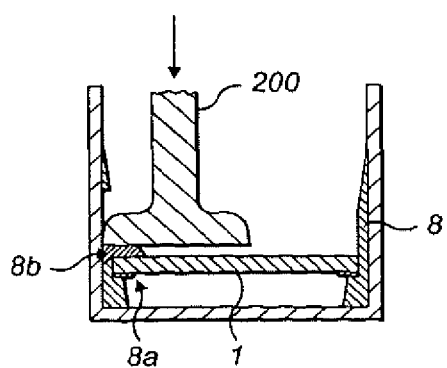
Figure 2D:
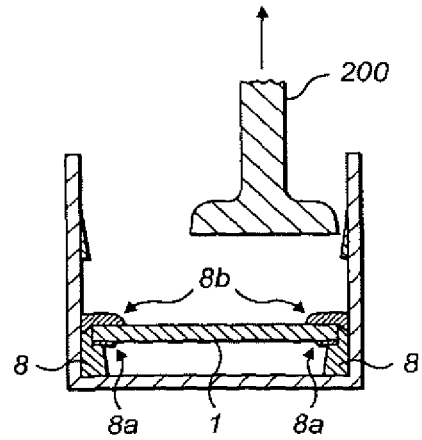

A "Biochip" is a general term for a reaction platform for hosting chemical, biochemical, proteomic or molecular tests, as may be required for medical diagnosis, drug detection, etc. Typically a Biochip comprises an inert substrate, such as silicon or glass (often of the order of about 1 $cm^2$ or less in surface area), on which one or a plurality of reaction sites is provided. The sites generally carry one or more ligands, selected for the test (or "assay") to be performed, adsorbed to the surface of the chip for activation upon combination with a sample applied to the chip (e.g. a blood sample) and/or a reagent. The reactions can be detected using a number of alternative techniques, including detection of chemiluminescence generated by the reaction. Some biochips carry a very large number (hundreds or thousands) of such tests sites, typically arranged in a grid or array, making it possible to carry out numerous assays simultaneously, and using the same single specimen. Some examples of Biochips available from Randox Laboratories Limited include:

Adhesion molecules Array
Antimicrobial Arrays
Cardiac Arrays
Cerebral Arrays
Cytokine Arrays
Drugs of Abuse Arrays
Fertility Hormone Array Growth Promoter Arrays
Ranplex CRC (Colorectal Cancer) Array
Synthetic Steroids
Thyroid Free Array
Thyroid Total Array
Tumour Monitoring Array
which in each case carry test sites configured to perform a set of tests relating to the indicated condition.

A first embodiment will now be described. This is a system designed to open individually foil sealed plastic wells. The system uses a strip of foil to seal and link a group of wells, this strip is then closed on itself to form a belt which is mechanically driven to both transport and peel open the well, freeing it from the foil belt. The chips are to be delivered in sets of a predetermined number (preferably more than 1, e.g. 10) of the same test array. It should be noted that the use of the term "foil" is not intended to imply that the strip comprises metal: examples of suitable materials will be given below.

FIG. 1 shows a specific exemplary design of a biochip well in a first embodiment. It should be noted that in the sealed well assemblies and apparatus for opening the sealed well assemblies, described below, any general tub or well shaped vessel, made for example of plastic, could be used. However, the design shown in FIG. 1 provides additional benefits, as will now be described, and is therefore preferred.

The biochip well shown in FIG. 1 is an Evidence Evolution™ Biochip by Randox Laboratories Ltd, and the Biochip 1 can be seen at the bottom of the well in the perspective view of FIG. 1(*a*). A biochip well having a biochip fitted therein is referred to hereinafter as a "biochip well assembly". FIGS. 1(*c*) and 1(*d*) are schematic plan and cross sectional views respectively, and here the location of the biochip 1 is indicated by dashed lines in FIG. 1(*c*). The well is defined by a vessel 2 formed of a rigid material such as injection moulded plastic. Inside the vessel, an open well is delimited by a base wall 2*a* and side walls 2*b* each formed by the vessel. The top of the well is an aperture 2*c* defined by the vessel and permitting access to the interior of the well. In this example, the aperture extends across the full area of the well, but this is not essential. Preferably, the vessel may include a tab 9, which can be used in the transportation of the well as described below. The tab 9 is a keying feature designed to co-operate with a robot arm forming part of the analyzer's transport mechanism. In use, the robot arm can clasp the vessel 2 by the tab 9, achieving a firm grip whereby the vessel 2 can be transported as necessary between stations in the analyzer. The ability to automatically convey individual vessels in this way makes the apparatus particularly suitable for randomized work loads, since the biochips do not need to be handled in a batch. Further, there is no requirement for any additional carrier component as used in conventional tray-type apparatus, thereby reducing the part count and reducing and simplifying the number of steps required for automatic production.

The vessel may also include a protrusion or boss 4 extending externally around the base of the well for use in guiding the movement of the vessel during opening, as will be explained below. This can also be used to retain the vessel in seats used to move the biochip between stations in the analyzer. Additionally, one or more button protrusions 4*a* may be provided on the external walls of the vessel for the same purpose. An example of their use is given below.

Inside the well is provided a retention means 8, which in this case takes the form of protrusions 8 extending towards the interior of the well from the side walls 2*b*. The protrusions 8 are interference fit features which, between them, are configured to grip a biochip 1 in use, and prevent its falling out or removal due to the friction between the features and the chip. The protrusions 8 thereby define a predetermined position at which the biochip will sit when it is inserted into the well (shown by the chip itself in FIGS. 1(*a*) and 1(*d*) and by the dashed line region in FIG. 1(*c*)). In this example, the protrusions are elongate ribs, extending up the side walls of the well. The depth of the ribs is greater towards the base of the well than at the top, as shown best in FIG. 2 (described below).

Alongside the predetermined chip position is a region 7 which is laterally offset from the chip in use. The chip does not extend into the region 7 due to its fixing in position by the retention means 8. In addition, in this example the region 7 is sized so as not to accommodate the chip: it will be seen that the region 7 has an approximately triangular cross section, decreasing in width away from the chip position 1. Thus, the chip cannot be inadvertently placed in the region 7 during assembly, and should the retention means 8 fail, the chip cannot slide into the region 7.

The laterally offset region 7 provides a space in the well into which a probe can be inserted via the aperture 2*c* for dispensation of sample or reagent, or evacuation of the well (e.g. removal of fluids) without risk of collision with the chip 1. This will be described in more detail with reference to FIG. 3, below. The region 7 includes a portion of the base wall 2*a* which is not covered by the chip 1 in use.

FIG. 2 shows steps which may be used in the manufacture of the biochip well assembly. Each of FIGS. 2(*a*) to (*d*) depicts a cross section of the well shown in FIG. 1, along the line I-I. Figure (*a*) shows the empty biochip well 2 and a biochip 1 held by the head of a vacuum tool 200 above the well 2. The vacuum tool is connected to a vacuum pump (not shown) which applies a suction force to the chip 1. Using the vacuum tool 200, the chip 1 is pressed into position between the protrusions 8. As shown in FIG. 2(*b*), the pressure may be such that portions of the protrusions are shaved by the edges of the biochip or otherwise buckle, resulting in compaction of some of the material forming the protrusion under the biochip in regions 8*a*. This not only ensures an exact fit between the chip periphery and the protrusions but also increases the stability of the chip by virtue of the "platforms" 8*a*.

In a next step, shown in FIG. 2(*c*), portions of the protrusions 8 above the biochip are deformed to form tabs 8*b* which extend a small distance over the top surface of the biochip 1. This could be achieved by heat, pressure or ultrasonic welding (or any combination thereof), but in the present example, the head of the vacuum tool 200 is used to apply pressure to the protrusion 8, causing it to buckle. The biochip is effectively "crimped" into place. This may or may not be repeated until all of the protrusions are deformed in this way, with the resulting assembly being depicted in FIG. 2(*d*).

Figure 3A:
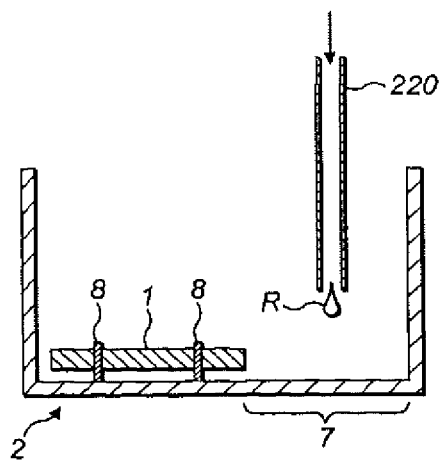
FIGS. 3(a) and (b) show exemplary steps of dispensing fluid in an analysis method.
Figure 3B:
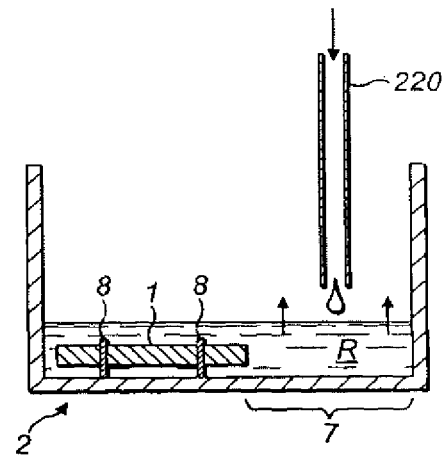
FIG. 3(c) shows an exemplary step of evacuating fluid in an analysis method.

As already mentioned, the laterally offset region 7 provides a location for off-chip dispensing or removal of fluids. FIGS. 3(*a*) to (*c*) are cross sections corresponding to that of FIG. 1(*d*) but with various details of the well removed for clarity. In FIG. 3(*a*), a dispensing probe 220 is pictured for dispensing reagent or sample (denoted R) into the well. It will be noted that the probe 20 is positioned above region 7 and not above the chip 1. The reagent or sample R is released into the well, and its level rises as shown in FIG. 3(*b*) until the chip 1 becomes submerged or at least covered by the fluid. Reaction between the reaction site(s) on the chip and the reagent or sample is thus initiated. By filling the well in this way, rather than dispensing the fluid directly onto the chip surface, the test sites on the chip surface each receive fluid of substantially the same concentration, thus reducing the potential effects of "trending".

Figure 3C:
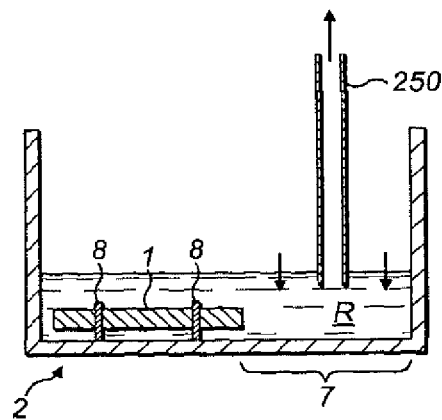

FIG. 3(c) shows a further step of the analysis procedure in which the volume of reagent or sample is removed from the well using a vacuum probe 250. The probe 250 is inserted into the body of fluid in the laterally offset region 7, away from the chip, an a pump actuated to draw fluid through the probe 250 and out of the well.

In both scenarios, as compared with conventional systems in which the position of the probe relative to the chip must be very precisely controlled (to ensure consistent trending and to avoid collisions), the requirements placed on the positional control of the probes 220/250 are very much reduced since they can be inserted at any location within the region 7 with the same results. The region 7 preferably has a surface area (in the plane viewed in FIG. 1(b)) of at least 20 mm$^2$: for instance, in the present example, the "triangular" region 7 may have a maximum internal width (nearest the chip 1) of around 8 mm and a length (between the chip 1 and the front of the well, adjacent tab 9) of around 5 mm. The greater the area of region 7, the lesser the positional accuracy required of the probe. However, the overall size of the well must be kept to within a usable limit. Further, the larger the well, the greater of volume of reagent/sample required to fill the well and submerge the biochip. In addition, the off-chip region 7 should preferably not be overly narrow in any one direction, since this too would require high positional accuracy. Preferably, the region has a length and width of at least 4 mm. For example, a rectangular region 4 mm by 5 mm would permit the insertion of a reasonably narrow probe, as would a circular region of around 4 to 5 mm in diameter. Thus it is preferable that the region 7 encompasses at least an area of this sort.

Figure 4A:
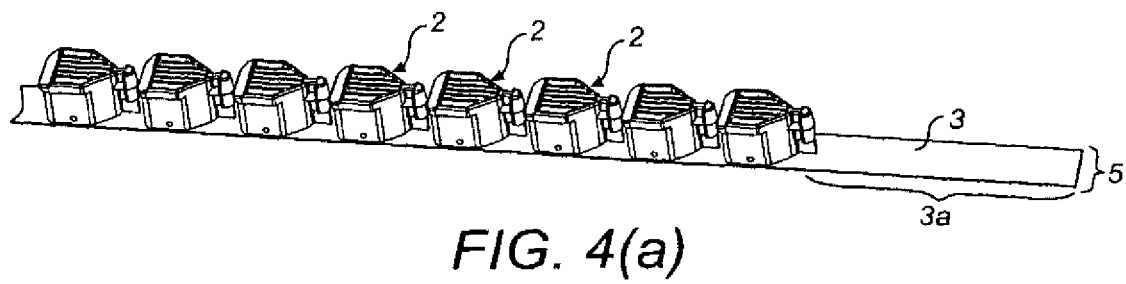
FIGS. 4(a) and (b) show two exemplary sealed well assemblies in an embodiment.
Figure 4B:
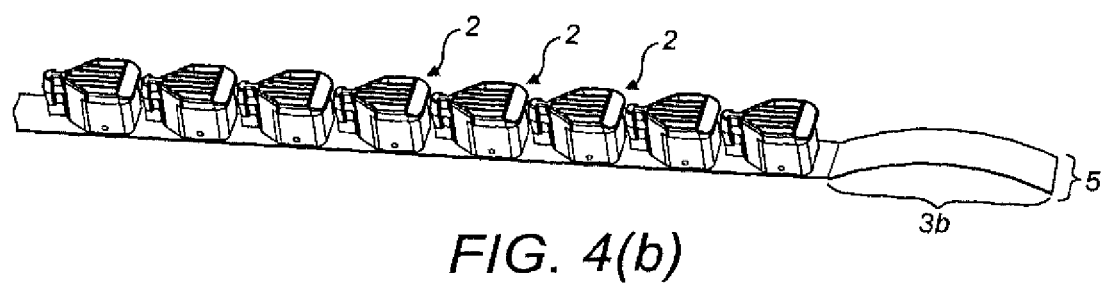
FIG. 4(c) is a schematic side view of an exemplary sealed well assembly.

FIG. 4 shows two examples of a embodiment of a sealed well assembly 5. A plurality of vessels 2 is arranged into a line or array. The vessels are preferably configured as biochip wells in the manner described above with respect to FIG. 1, although this is not essential. As an example, a set consisting of ten such wells 2 in an end-to-end configuration will be used in the present embodiment. Conceptually a side-by-side arrangement would work equally as well as the nose-to-tail arrangement depicted. Two dimensional arrays of wells 2 could also be used in some cases: for instance if two biochips are to be dispensed simultaneously the set could consist of a 2×n array. Any other number of wells could alternatively be used in the stack.

In use, each of the wells contains a biochip and typically all of the wells in one sealed well assembly 5 would contain the same type of biochip (i.e. configured for performance of a particular assay type). However this is not essential and indeed where the set is a two dimensional array, it may comprise lines of different chip types, e.g. such that two chips dispensed simultaneously are of two different selected test types.

The line or array of wells 2 are affixed, preferably by heat sealing, to a specialized sealing sheet or "strip" 3 as depicted in FIG. 4. Any suitable sealing material could be used to form the strip 3 but in this example it is a metal foil. In other examples, the strip 3 may comprise one or more polymer and/or cellulose-based layers, or a metallised foil such as a polymer and metal foil laminate. The foil used is coated to provide a heat sealable surface, e.g. with polypropylene, polyethylene or polystyrene, or a combination thereof. It is foreseeable that alternative methods could be used, e.g. adhesives or ultra sonic welding, to achieve a similar mechanical join and environmental seal.

The strip 3 extends some distance ahead and/or behind the line of wells 2, in the same direction as the line. This enables the strip 3 to be driven (or otherwise controlled) by a well opening apparatus, as will be described below. In the FIG. 4 embodiment, the strip 3 has one extension region 3a in front of the vessels, and another 3b at the rear of the line. However, in other embodiments one or the other may be omitted. Each extension region is configured to have sufficient length for co-operating with the well opening apparatus as described below. For instance, in one example, the or each extension region may have a length (in the direction parallel to the line of wells) at least equal to that of one of the vessels 2. In another example, the or each extension region may be at least 1.5 cm long, more preferably at least 2 cm long and still preferably at least 5 cm long to enable the strip to be wound onto a spool or otherwise gripped.

Figure 4C:
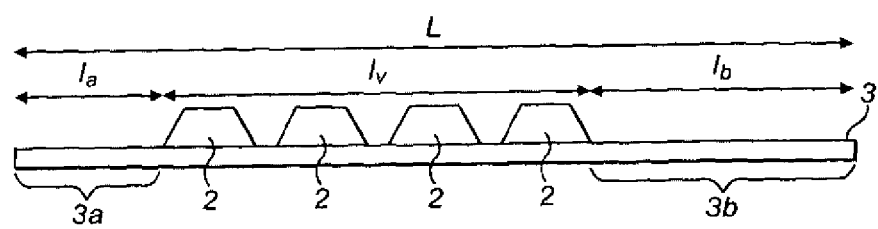

In the present embodiment, the combined length of the extension regions 3a and 3b is approximately equal to (or greater than) the length of the strip 3 on which the vessels 2 are carried. This is depicted in FIG. 4(c). In this example, the strip 3 is equipped with four vessels 2 arranged one behind the other. The total length of the strip region carrying the vessels (from the front of the first vessel to the rear of the last vessel) is denoted $l_v$. The extension region 3a at the front of the strip has a length $l_a$, and the extension region 3b at the rear of the strip has a length $l_b$, where $l_a$ need not be equal to $l_b$ (although this is an option). The combined length of the two extension regions $(l_a+l_b)$ is approximately equal to or greater than $l_v$. Thus the total length of the strip, L, is approximately equal to or greater than $2×l_v$.

Embodiments of this type are preferred since the long extension regions permit the strip 3 to be formed into a closed loop around a guide plate as will be described below. However, in practice this can also be achieved with shorter extension regions if a clip or other component is provided for holding the two ends of the strip (preferably in fixed relation) to complete the loop.

Figure 5:
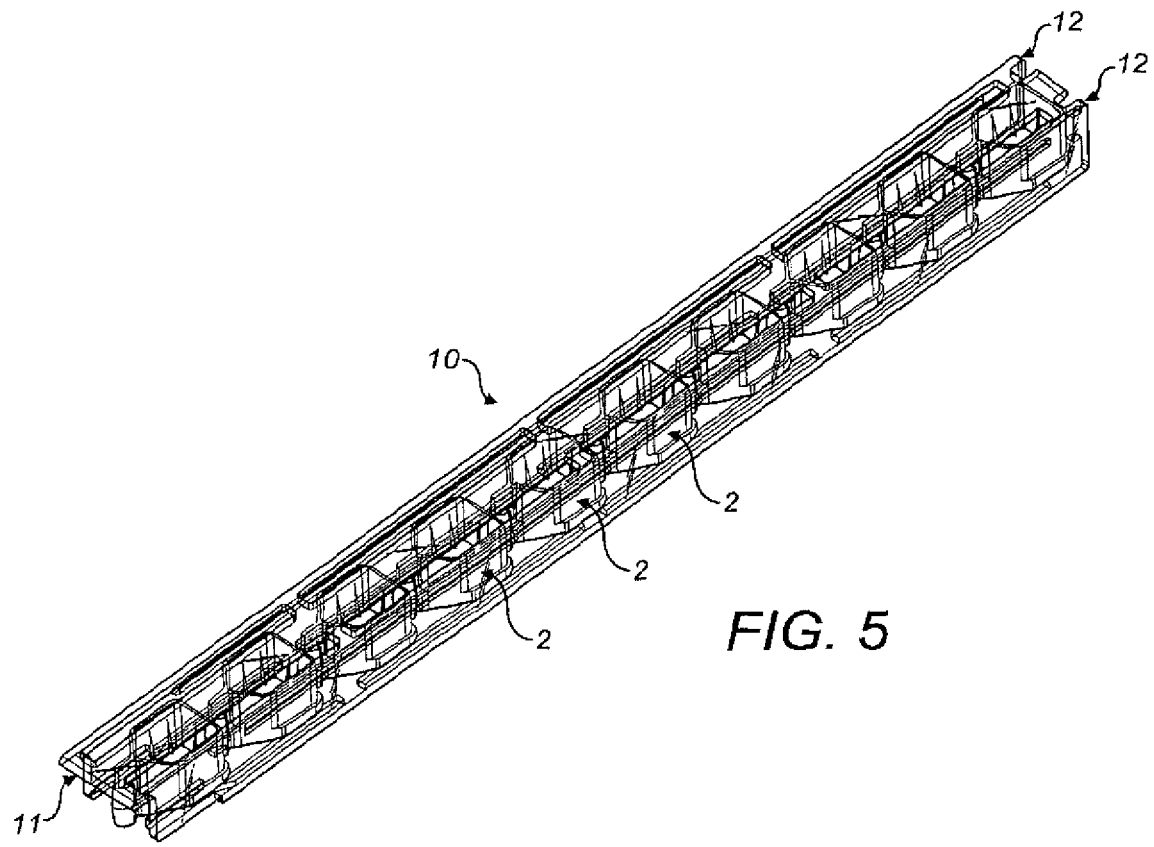
FIG. 5 depicts an embodiment of a cartridge showing a plurality of biochip wells inside the cartridge for reference.

The strip with wells attached forms a unit referred to as a sealed well assembly 5. The sealed well assembly 5 could be loaded directly into an apparatus for opening the vessels, such as those discussed below with reference to FIGS. 12 to 17. However, in the present embodiment, the sealed well assembly 5 is entered into a cartridge 10 which serves as a transport device, offering protection to the wells and foil during handling and transport, and as a means to conveniently load the set of wells into the analyzer, as well as providing a guide structure which takes part in the opening of the wells, as described below. A first embodiment of the cartridge 10 is depicted in FIGS. 5 and 6.

The cartridge 10 comprises a guide structure for accommodating the plurality of vessels 2 therewithin and constraining the vessels to move along a predetermined path upon dispensation. In this example, the cartridge is substantially "U"-shaped in cross-section, comprising a guide plate 11, towards which the open faces (apertures) of the vessels 2 face in use, and two side walls 12 extending orthogonally from the guide plate 11 either side of the line of vessels 2. This is best seen in FIG. 5, which shows the vessels 2 inside the cartridge 10, with the sealing strip 3 removed for clarity, and in FIG. 6, which shows the empty cartridge 10.

Figure 6:
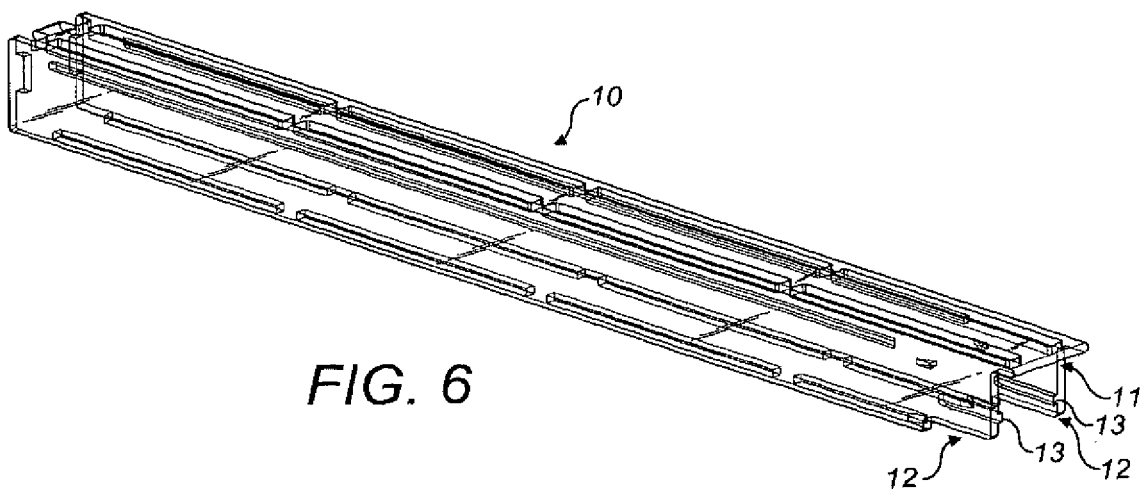
FIG. 6 illustrates the cartridge of FIG. 5, empty.

From FIG. 6, it can also be seen that an elongate guide channel in the form of protrusions 13 is provided on the inside of the side walls 12 adjacent one end of the cartridge 10. As described further below, these assist in the opening of the vessels 5.

Figure 7:
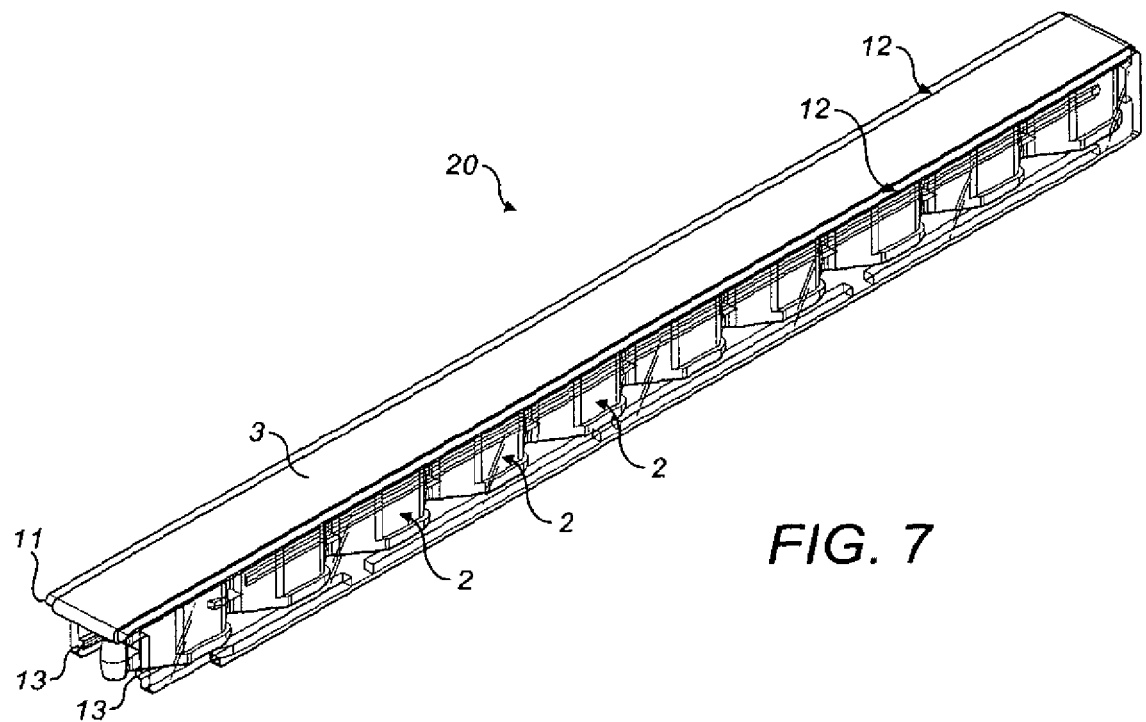
FIG. 7 depicts an embodiment of a cartridge assembly.

In this example, the two ends of the foil strip 3 are joined to themselves to form a closed loop or belt around the cartridge 10, as shown in FIG. 7. This could also be achieved by heat sealing, ultrasonic welding, mechanical crimping, with adhesives or using a mechanical clip of which an example will be described below. In the present example, the loop encloses only the guide plate 11 of the cartridge although other arrangements are possible as will be discussed below. The combination of the cartridge 10 and sealed well assembly 5 (whether or not the sealing strip is formed into a loop) forms a unit referred to hereinafter as a cartridge assembly 20.

Figure 8:
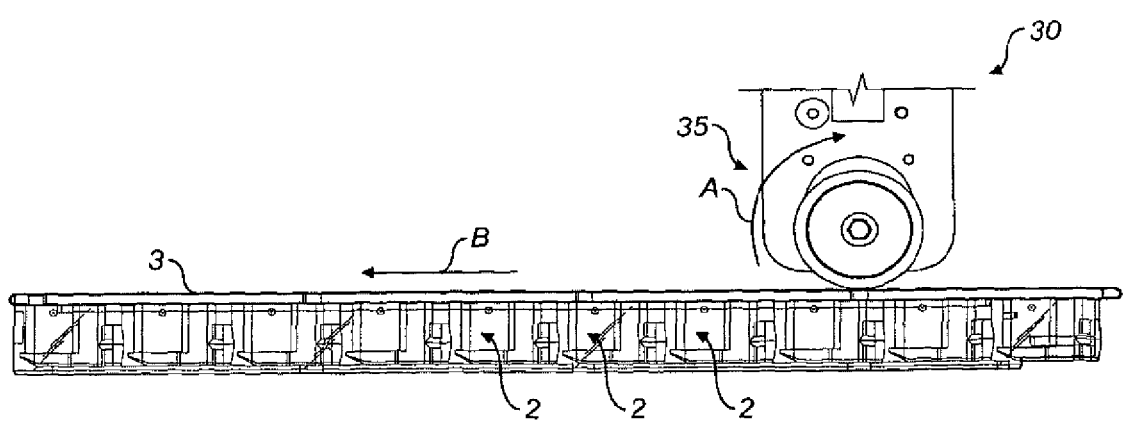
FIG. 8 schematically depicts a first embodiment of an apparatus for opening sealed wells.

A first embodiment of an apparatus 30 for opening sealed wells is depicted in FIG. 8. In this example, part of the apparatus 30 is formed by a cartridge assembly 20 as described above. However, this is not essential since the functions of the (removable) cartridge assembly could be performed by other components provided to the apparatus 30. A drive mechanism 35 such as a driven rubber wheel is actuated against the foil 3 and has the effect of transporting the foil belt 3 around the cartridge housing 10. In FIG. 8, arrow A indicates the direction of rotation of the rubber wheel, and arrow B indicates the resulting motion of the (top portion of) the foil belt 3.

Figure 9:
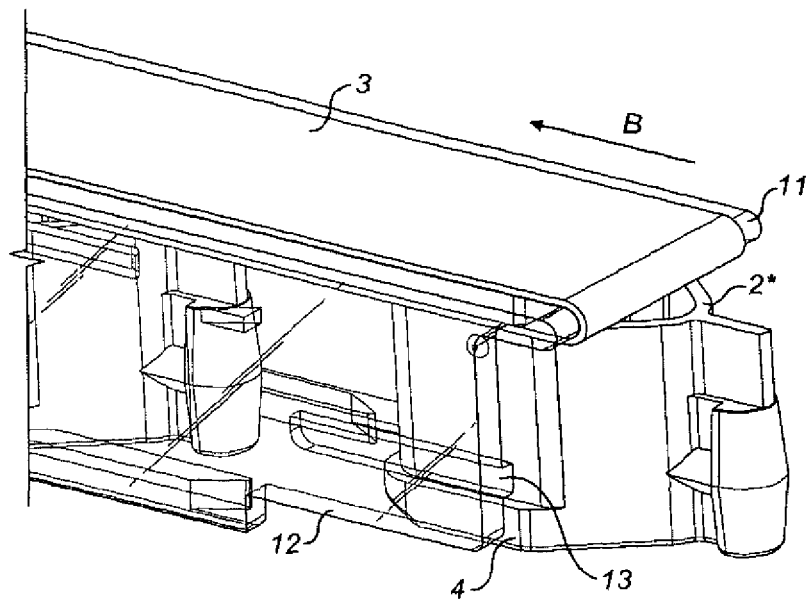
FIG. 9 is an enlarged detail of FIG. 8.

Since the movement of the vessels 5 is constrained by the guiding structure of the cartridge 10 (such that they can only move along the long axis of the cartridge, or parallel to the original plane of the foil), as the frontmost well 2* passes the edge of the cartridge, the foil is peeled away from it. This is shown in FIG. 9. The apparatus therefore opens and continues to drive the well forwards until the seal is completely broken. This has the added benefit that the waste foil is retained on the cartridge 10 in a single piece making disposal simple. The well enters a guided channel before it reaches the edge of the cartridge preventing it from rotating. In the present example, this takes the form of elongate protrusions 13 disposed on the interior of the cartridge side walls 12, which cooperate with a laterally offset protrusion 4 on the sides of the vessels 2. Of course, other keying features could be used instead.

Figure 10:
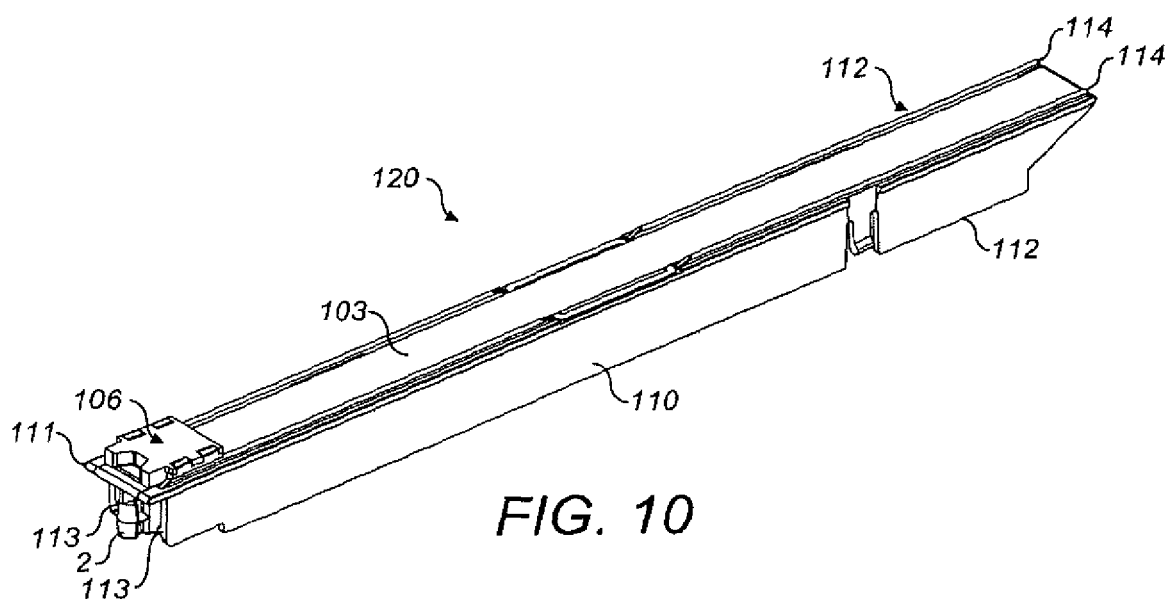
FIG. 10 shows a further embodiment of a cartridge assembly.
Figure 11:
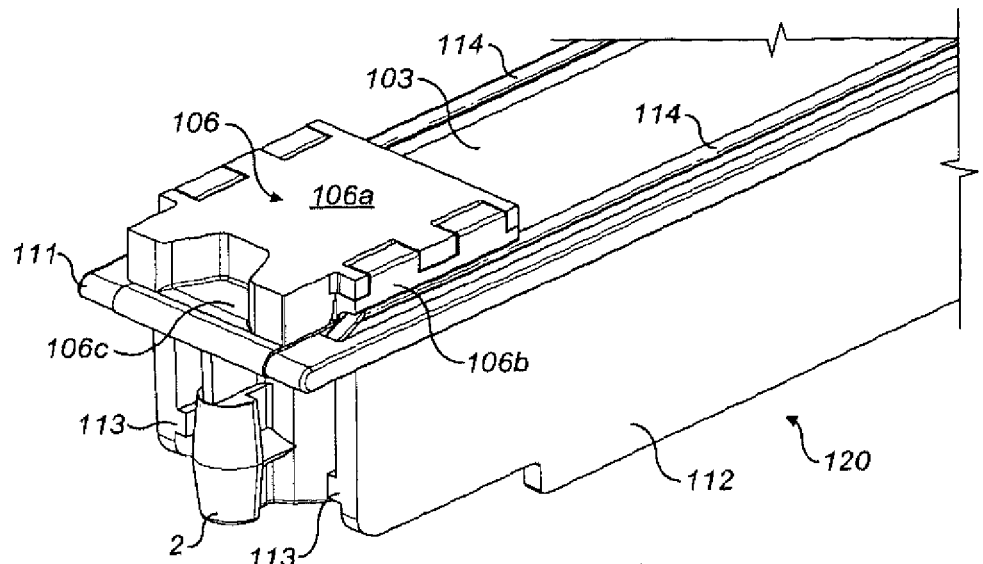
FIG. 11 is an enlarged detail of FIG. 10.

FIGS. 10, 11, 12 and 13 show components of an alternative embodiment. FIGS. 10 and 11 show a cartridge assembly 120 comprising a cartridge 110 which is substantially identical to cartridge 10 discussed above, having a guide plate 111 and two orthogonal side walls 112 as well as guide channel protrusions 113 (shown best in FIG. 11). On the outer surface of guide plate 111, two lateral guide runners 114 are also provided for maintaining the position of sealing sheet (foil) 103. The sealing sheet 103 forms part of a sealed well assembly which is identical to that discussed above in connection with FIG. 4, including a series of wells 2 (of which only the frontmost is visible in FIGS. 10 and 11).

As in the preceding embodiment, the sealing sheet 103 is formed into a loop around the guide plate 111. In this example, this is achieved using a mechanical clip 106 which sits against the outer surface of guide plate 111. The clip 106 comprises an interior plate 106b, which is inserted between the foil 103 and the guide plate 111, and an exterior plate 106a which carries snap-fit features for engaging the interior plate. The two plates 106a and 106b are closed over the two ends of the foil 103 such that each is retained within the clip to form a continuous loop. In one example, the two plates are hinged together at one side so that the two foil ends can be placed between the hinged plates which are then snapped shut to hold the ends in position. It should be noted that the two ends of the foil may or may not overlap one another inside the clip 106. If not, the clip 106 itself completes the closed loop path.

The clip 106 is configured to travel along the exterior of cartridge 110, conveying the foil 103 with it. To assist in guiding the clip 106, its sides are preferably configured to accommodate the guide runners 114 as shown best in FIG. 11. The clip 106 also includes a keying feature 106c for co-operating with a drive mechanism, as will now be described. However this is not essential and a drive mechanism such as a driven wheel as already described could alternatively be used to contact the foil 103 rather than the clip 106.

Figure 12:
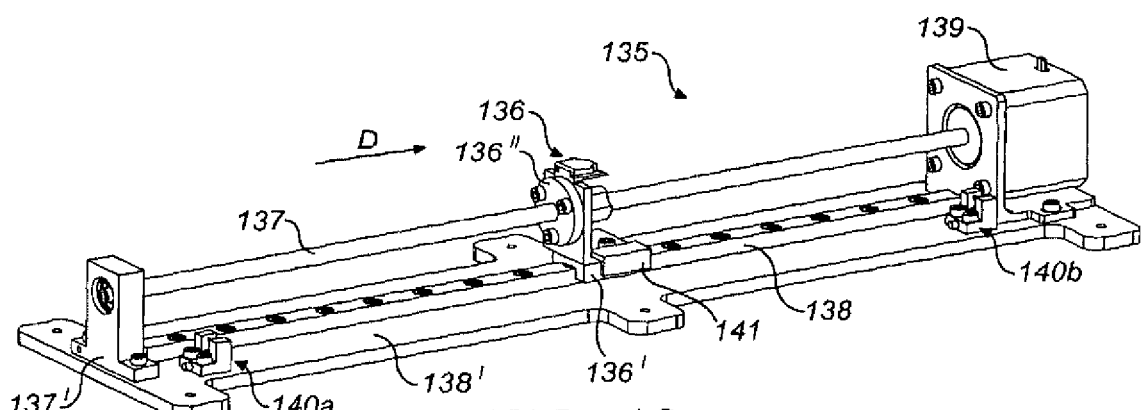
FIG. 12 shows an exemplary drive mechanism used in a second embodiment of an apparatus for opening sealed wells.

FIG. 12 shows a drive mechanism 135 suitable for use in combination with the cartridge assembly 120 described above as an apparatus for opening the sealed wells. In use, the drive mechanism is positioned in line with the cartridge assembly 120 with its uppermost components (as viewed in FIG. 12) facing the exterior surface of guide plate 111 (on which the clip 106 sits).

The drive mechanism 135 comprises a drive block 136 which is adapted to contact the clip 106 of the cartridge assembly as will be described further below. The drive block 136 is mounted on a threaded shaft 137 which passes through an aperture in the drive block provided with an internal thread (not shown). One extremity of the drive block 136 slidably engages with a guide rail 138 which extends parallel to the threaded shaft 137. The guide rail 138 typically forms part of a mounting plate 138' for mounting the drive mechanism 135 to an analyzing apparatus. At one end of the mechanism, a motor 139 is provided for rotatably driving the threaded shaft 137. The other end of the threaded shaft is held in bearing block 137', which permits its free rotation. In use, rotation of the shaft 137 causes the drive block 136 to move in a straight line along the drive mechanism in the direction indicated by arrow D.

At each end of the drive mechanism are provided sensors 140a and 140b for detecting the position of the drive block. In this example, each sensor is a light gate (comprising a light emitter and a light receiver), and the drive block carries a flag 141 positioned to obstruct transmission of light between the sensor components when the drive block reaches the relevant position. Connections are provided between the sensors and a controller (not shown), which also controls motor 139 to ensure that the drive block is not driven beyond is operating range.

Figure 13A:
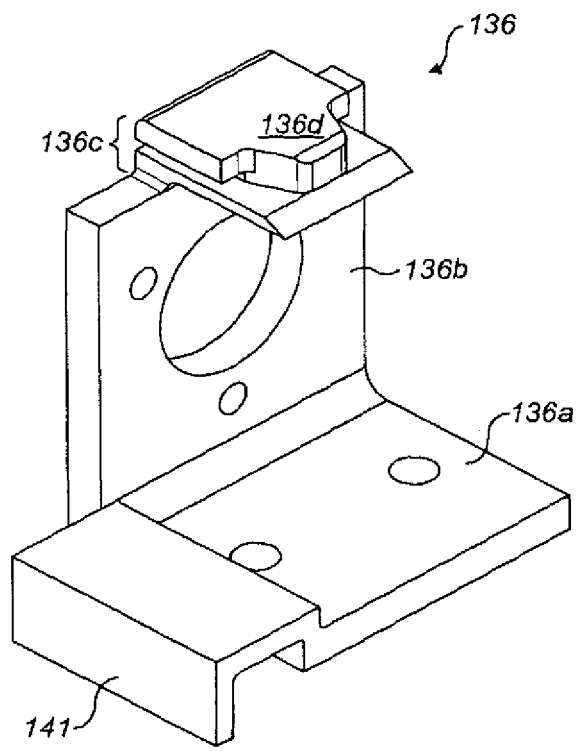
FIG. 13(a) shows a drive block component of the drive mechanism of FIG. 12.
Figure 13B:
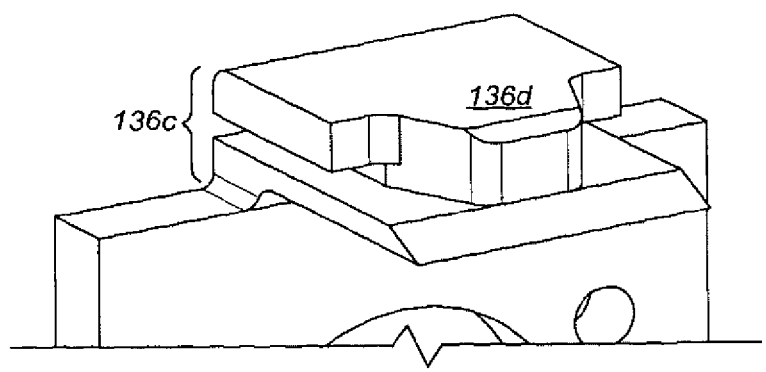
FIG. 13(b) shows a detail of FIG. 13(a)
Figure 14:
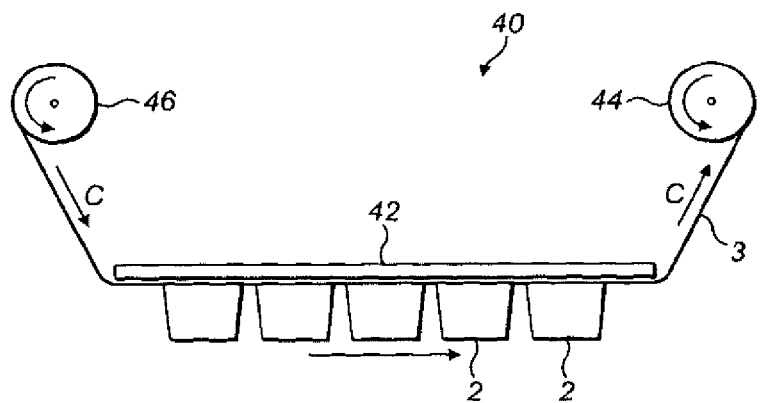
FIG. 14 schematically depicts a third embodiment of an apparatus for opening sealed wells.

FIG. 13a shows the body of drive block 136 in more detail. In use, the drive block 136 is mounted to the drive mechanism via a carriage 136' which slidably engages guide rail 138, and an aperture plate 136" which carries the aforementioned internal thread for engagement with threaded shaft 137. The drive block itself comprises a metal or plastic body having a base 136a, an upright panel 136b and a head 136c protruding towards the intended direction of motion. On the top of head 136 is carried a keying protrusion 136d which is shaped to fit with keying feature 106c provided on the clip 106 of the cartridge assembly 130.

In use, if the cartridge assembly is full, the cartridge is loaded into position relative to the drive mechanism with the drive block positioned at the position furthest from motor 139 (adjacent sensor 140a). The drive block is driven forward (in the direction of arrow D) until it engages with clip 106 of the cartridge assembly, which will preferably be in the position shown in FIG. 10, at one extremity of the cartridge. When a biochip is to be dispensed, a controller actuates motor 139 for a predetermined duration (or, alternatively, until appropriate sensing signals are received from sensor 140a or another sensor provided along the path), such that drive block pushes the clip 106 along the cartridge by a certain distance. The foil belt 103 travels with the clip 106, conveying the frontmost well 2 out of the cartridge and releasing the vessel from the foil strip in the same manner as discussed above with reference to FIG. 9. The vessel can then be collected by a transport mechanism and conveyed to a test position at which sample analysis will be carried out using the biochip within the well.

The motor is halted until a further dispensation instruction is received, at which point the process is repeated and another well dispensed. This continues until the entire sealed well assembly has been dispensed at which point the empty cartridge can be removed from the apparatus and replaced with a new one.

Some further embodiments of apparatus for opening sealed well assemblies will now be described with reference to FIGS. 12 to 16. In each case, the sealed well assembly is as described above in connection with FIG. 4, except where otherwise indicated. Each embodiment may or may not make use of a cartridge.

Firstly, a system using an open loop where the front tail of the foil 3 is actuated is envisaged. For example, a third embodiment of an apparatus 40 for opening sealed wells is shown schematically in FIG. 14.

In this example, the sealing sheet 3 is fitted between two rollers 44 and 46, one of which drives the leading (front) end of the strip 3 forward and the other is an idler, controlling the trailing end of the strip 3 and, optionally, applying tension. The wells 2 will be opened in the same way as the first embodiment when they reach the edge of the guide structure 42.

This embodiment could be implemented using a cartridge arrangement as described above to guide the path of the vessels 2 and of the sealing strip 3. In this case, the guide structure 42 would correspond to the guide plate 11 of the cartridge described above. However, if preferred the guide structure 42 can alternatively take the form of a permanent fixture of the apparatus 40. Depending on the precise geometry, the guide structure 42 may simply comprise a plate performing the same function as guide plate 11. However in preferred cases, additional guiding features (not shown) for performing the functions of side walls 12 and particularly guide channel 13 in the region where the frontmost well is opened, will be provided. In use, the sealed well structure comprising the vessels 2 and strip 3 will be inserted into the apparatus and fitted to the drive components 44, 46 around the guide structure 42.

Figure 15A:
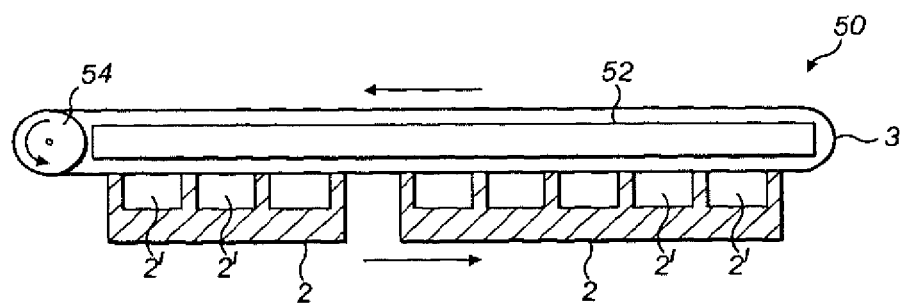
FIGS. 15(a) and 15(b) schematically depict a fourth embodiment of an apparatus for opening sealed wells.
Figure 15B:
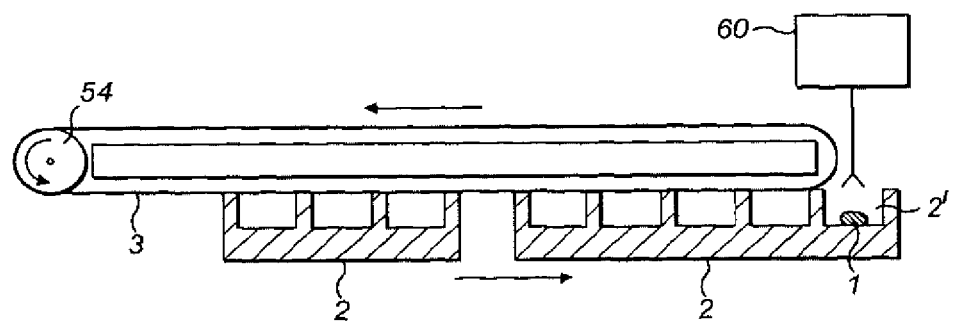

It should be noted that the vessels 2 need not be individual—for example, more than one well 2' could be defined in a single vessel 2, as shown in FIGS. 15a and 15b in a fourth embodiment of an apparatus 50 for opening sealed wells, for example.

Again, by controlling the amount by which the sealing sheet 3 is driven forward, only a single one of the wells 2' (or more if desired) need be opened. A device 60 can be provided for taking the biochip 1 out of the well if required, such as a robotic arm.

This embodiment also implements the drive mechanism differently, using a driven roller 54 arranged inside the looped sealing sheet path. In alternative embodiments, the sealed well assembly 20 could be driven by applying drive means to the vessels 2 rather than the sheet 3 (which will indirectly drive the sheet 3).

Again, the guide structure 52 in this case may be provided by a removable cartridge or could form a permanent part of the apparatus 50. If a cartridge arrangement is used, the drive roller 54 could form part of the cartridge and include connection means for transferring drive to the drive roller from an external motor included in the apparatus 50.

Figure 16:
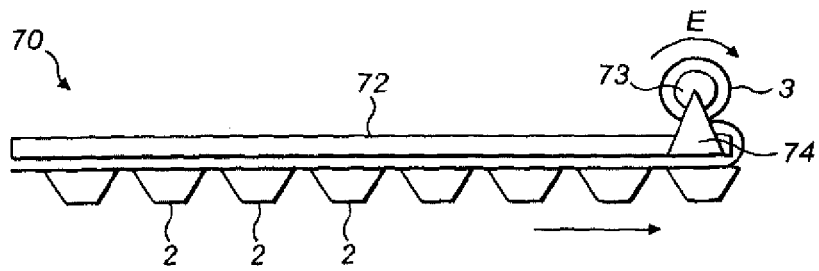
FIGS. 16, 17 and 18 show selected components of apparatus for opening sealed wells in further embodiments.

FIG. 16 shows another embodiment in which the sealing sheet 3 is not formed into a closed loop. Instead, the leading edge of the sheet 3 is wound onto a spool or wheel 73 fixed relative to guide plate 72. Preferably, the guide plate 72 is provided by a cartridge and the spool 73 is disposed on the cartridge via a mount 74. The spool 73 is preferably driven through a connection to a motor disposed off the cartridge. Winding the spool 73 in the direction shown by arrow E conveys the wells 2 forward and releases the frontmost well in the same manner as previously described. To maintain tension, the trailing edge of the foil 3 may be controlled, for example by biasing it away from the spool 73.

Figure 17:
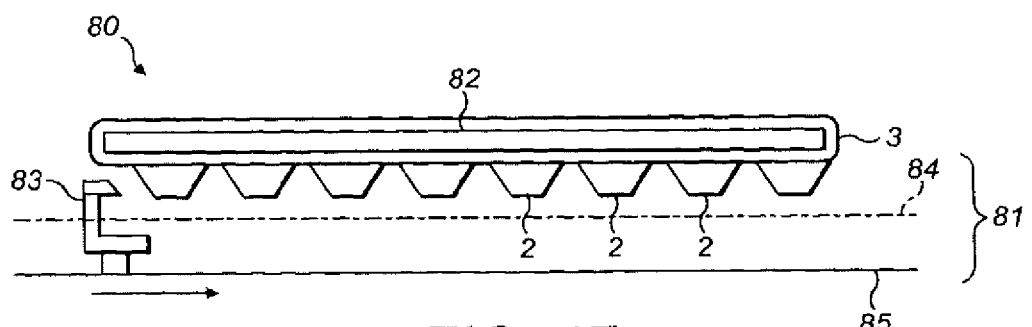

In FIG. 17, an embodiment is depicted in which drive is applied to one of the vessels rather than directly to the sealing sheet 3. Here, the foil 3 is formed into a closed loop around the guide plate 82 as in previous embodiments. The drive mechanism 81 is similar to that shown in FIG. 13: a drive block 83 is mounted on a threaded shaft 84 and travels along a guide rail 85 upon rotation of the shaft 84. The drive block engages one of the wells 2 and moves it forward, thereby also conveying the foil 3 around its looped path. The frontmost well 2 is released in the same manner as previously described. It should be noted that the drive block may be configured to push or pull the well 2, and it need not be the frontmost well which is engaged. Indeed, it is preferred that the drive block engages the rearmost well.

Figure 18:
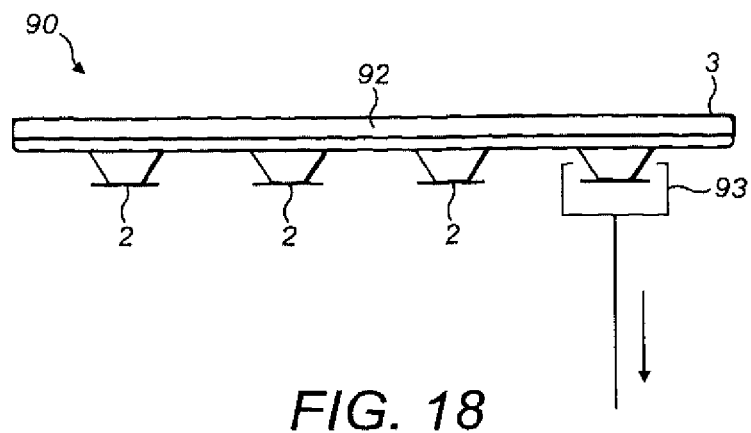

FIG. 18 shows a comparative example of an apparatus which can also be used to open sealed wells of the sort described above. In this example, the sealing sheet 3 is preferably fixed in position (e.g. clamped or sealed to the guide plate 92). A mechanical grabber 93 approaches the sealed well assembly and engages with one of the wells 2. The wells may be provided with additional keying features for this purpose. Once engaged, the grabber 93 pulls the well 2 in an approximately orthogonal direction away from the sealing sheet 3, to thereby release the well. This has the advantage that the wells can be released in any order, but suffers from disadvantages in that the force required to release the well is comparatively high (or conversely the seal between well and sheet must be comparatively weak).

In all of the above embodiments, the apparatus for opening the sealed wells may typically form part of an analyzer. The drive means can be actuated by a controller receiving instructions from the analyzer as to when to dispense one of the wells, and how many. Several such well opening apparatus may be provided in any one analyzer.

FIGS. 19(a) to (f) depict an embodiment of an apparatus designed to dispense wells from multiple sealed well assemblies. This is desirable since typically each sealed well assembly will contain biochips of a single type, and the analyzer may be required to perform many different tests, in an arbitrary order. Apparatuses of the sort described in the present embodiment enable "on demand" provision of chips from any of multiple different sealed well assemblies, in any order.

Figure 19A:
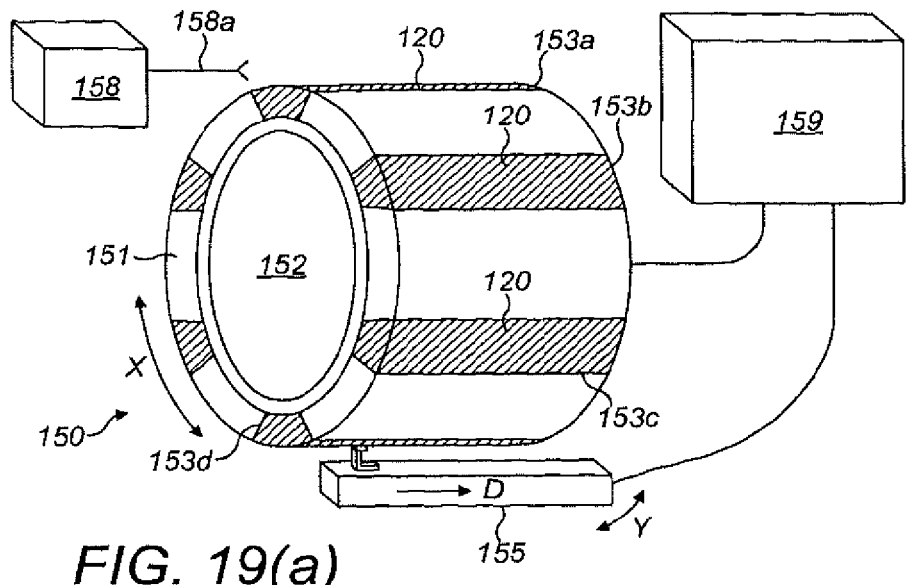
FIGS. 19(a) to (f) show portions of another embodiment of an apparatus for opening sealed wells, alongside components of a transport mechanism for transporting the opened wells.
Figure 19B:
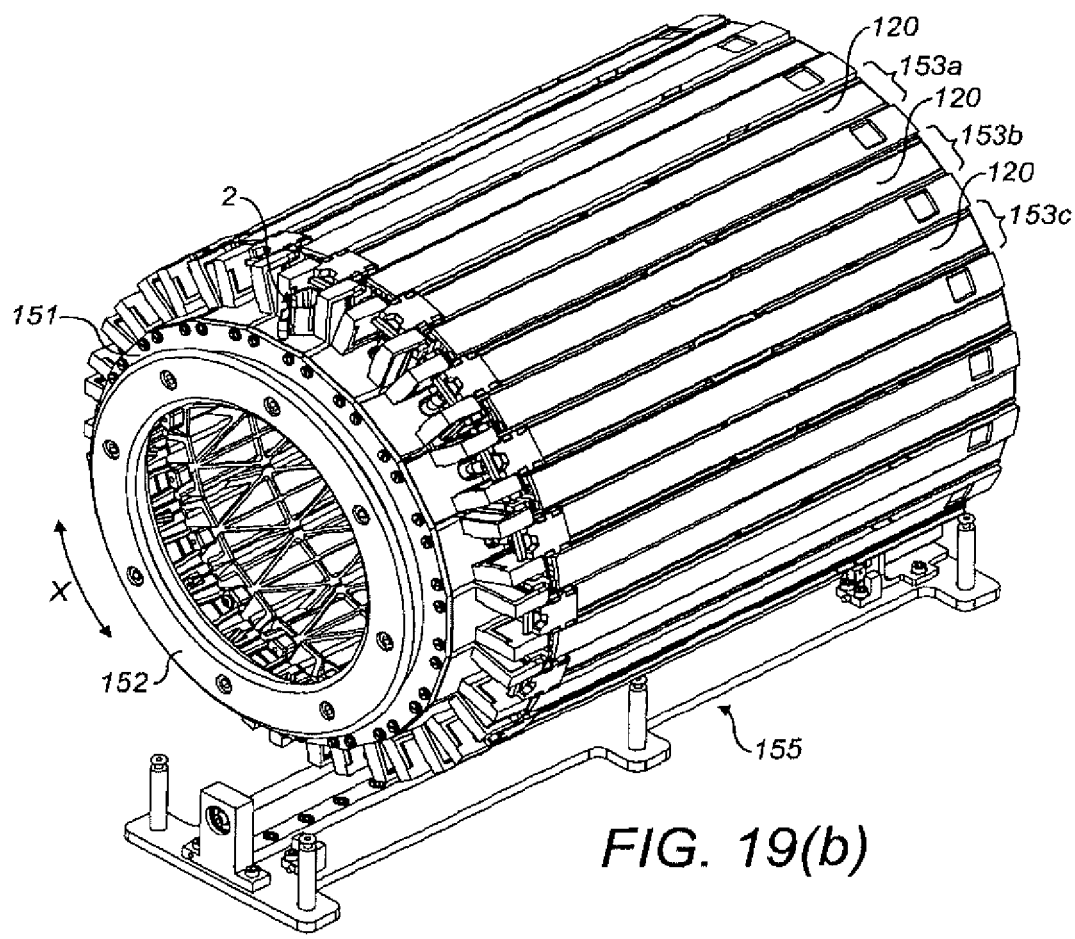
Figure 19C:
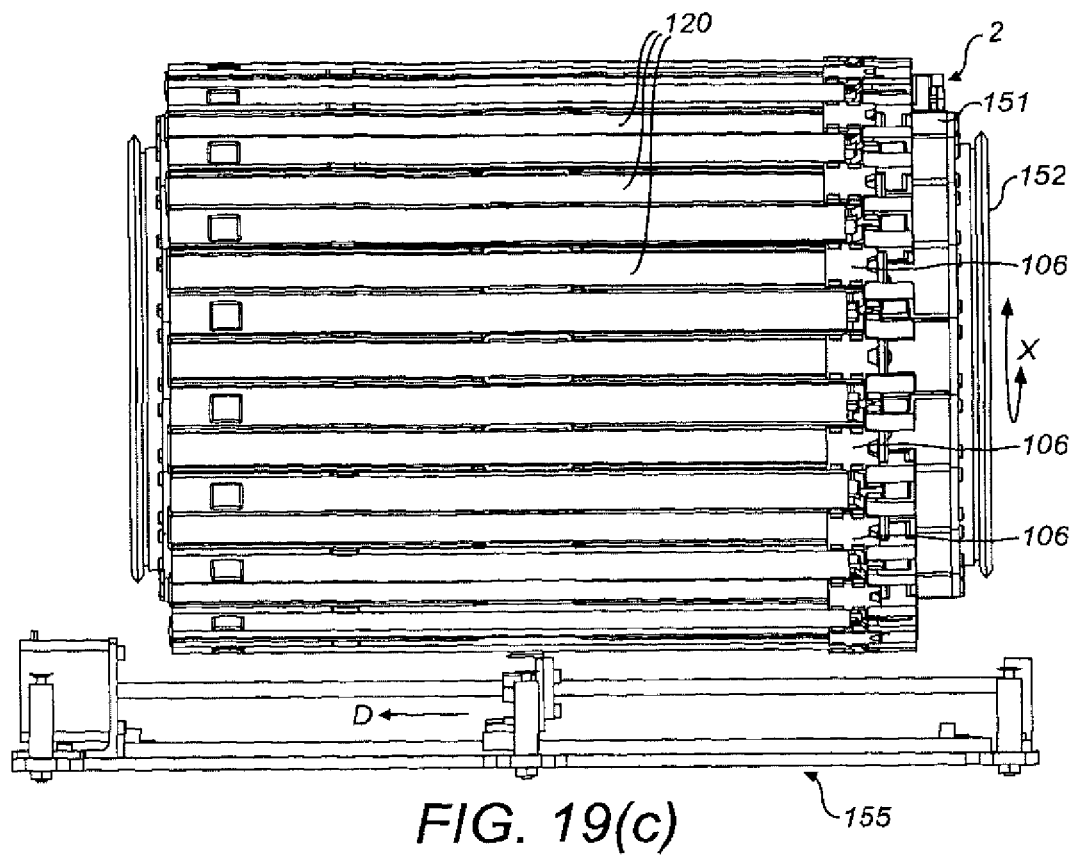
Figure 19D:
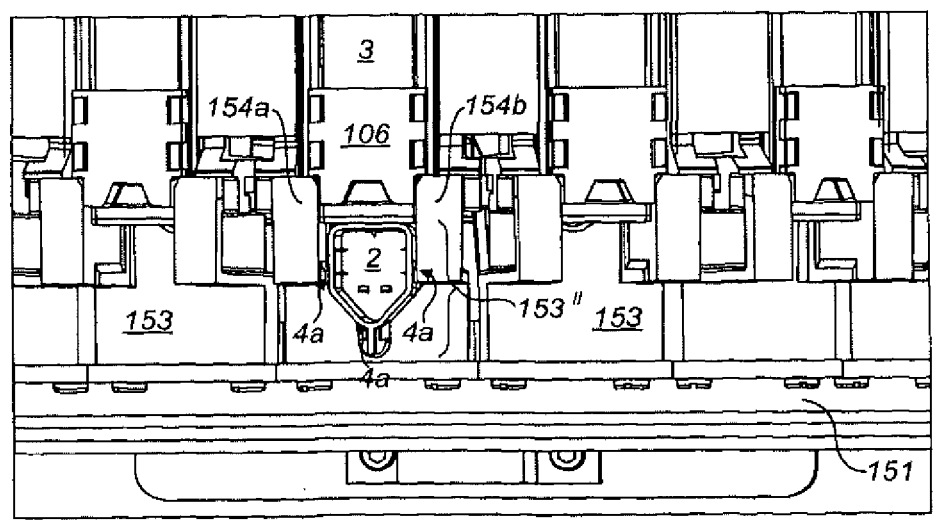
Figure 19E:
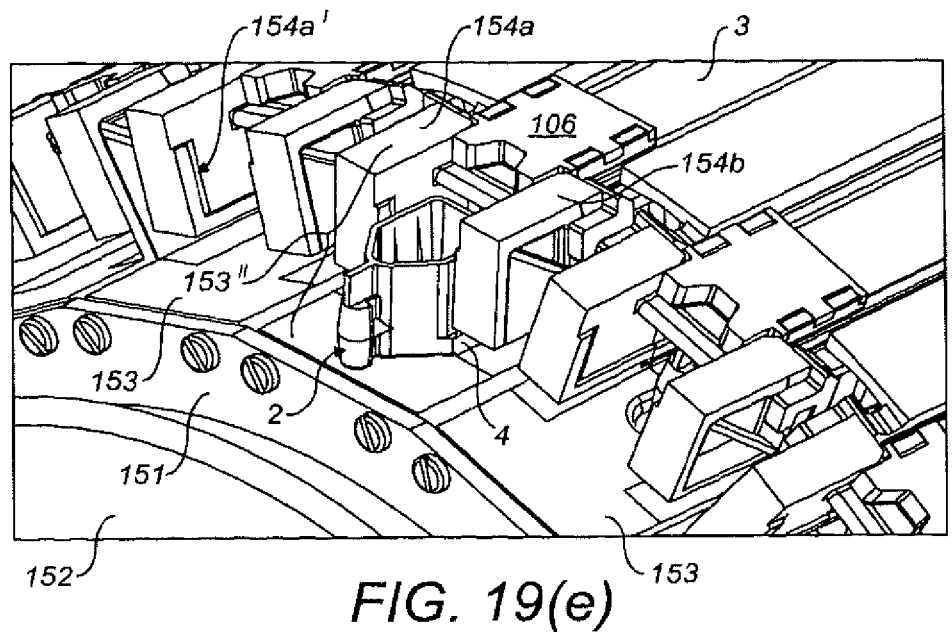
Figure 19F:
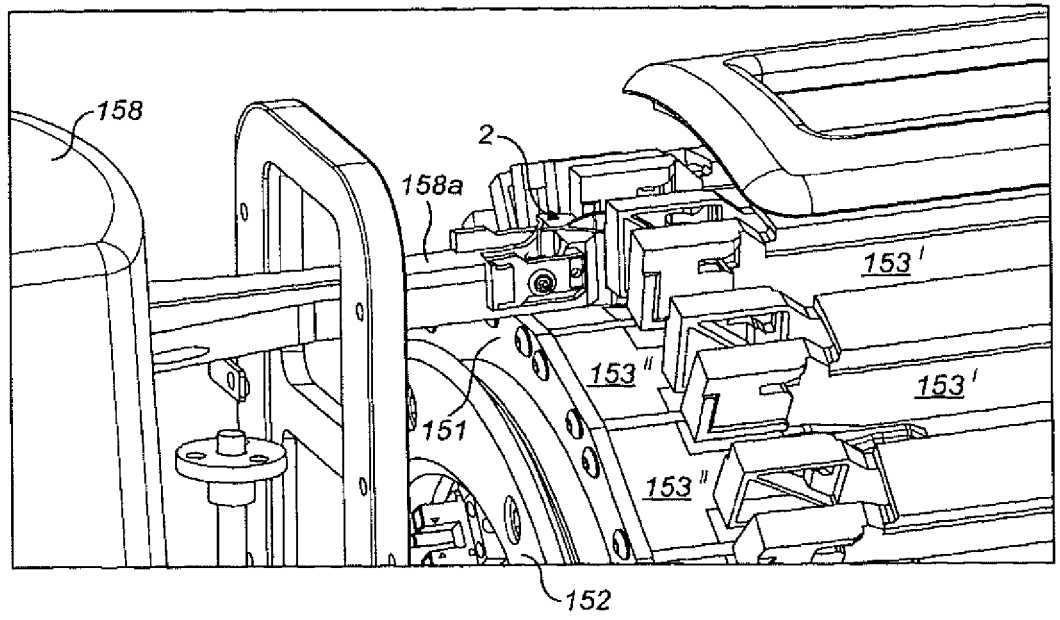

Selected modules of the apparatus 150 are shown schematically in FIG. 19(a). A support or "barrel" 151 carries a plurality of cartridge assemblies such as 120 shown in FIG. 10 in cartridge holders 153, of which only four are labelled in FIG. 19(a) for clarity (items 153a, 153b, 153c and 153d). In this example each cartridge assembly 120 is substantially as described above with respect to FIGS. 10 and 11, although any of the other embodiments could also be utilized instead. Further, permanent guide structures could be used in place of the (removable) cartridges, in which case the sealed well assemblies would be fitted directly to the support 151.

In this example, the support 151 takes the form of a barrel in which the cartridges holders 153 are arranged on a cylindrical surface, the long axis of each parallel to the long axis of the cylinder. This is convenient since the support 151 can be rotated about its long axis to select a different one of the cartridges for dispensing as described below. However, in other implementations the support could be a planar array of cartridges, or a column of stacked cartridges, or even a three dimensional array having both columns and rows.

The support 151 is carried on a core 152 inside the cylinder of cartridge holders, supported by bearings. The core 152 may include one or more cogs configured to mesh with corresponding teeth provided on the inside of support 151, which when driven by a motor (also contained within core 152) rotate the support 151 in the desired direction X.

Alongside the support is provided at least one drive mechanism 155 positioned so as to cooperate with at least one of the cartridges. In this example, the drive mechanism 155 is as described with reference to FIG. 12 above. However, any of the aforementioned embodiments could be utilized instead. If desired, a dedicated drive mechanism can be provided for each of the cartridges (indicated in FIG. 19(*a*) by dashed lines) However, in the present embodiment, several (or all) of the cartridges are served by the same drive mechanism 155, which is movable relative to the support 151. Relative movement may be achieved by rotating the support about its long axis (arrow X) and/or by movement of the drive mechanism (carried for instance on an outer drum, not shown). In other implementations, such as the planar or column type support mentioned above, the drive mechanism may sit alongside the support and relative motion could be achieved through mounting the drive mechanism and/or the support on a linear actuator. Appropriate sensors may be provided for detecting the position of the drive mechanism 155 relative to the support.

In the present example, the drive mechanism 155 is located underneath the support 151, at a position in which it can engage with and drive a cartridge assembly loaded into the lowermost cartridge holder 153*d*. Thus when a biochip well is to be dispensed, the cartridge assembly 120 containing the desired biochip well is identified and the support 151 is rotated until the identified cartridge assembly is positioned at the location indicated by holder 153*d* in FIG. 19(*a*). The drive mechanism 155 is then actuated in the manner previously described such that it engages with the selected cartridge assembly (e.g. through drive block 156) and conveys the vessels or sealing strip such that one vessel is released. The drive mechanism is then disengaged and the support 151 is once again rotated to a position in which the released biochip well can be collected. In this is example, the well is collected by a transport module 158 including a robotic arm 158*a* located at the top of the barrel 151. Thus, the barrel is rotated through approximately 180 degrees in order that the selected cartridge and the one released biochip well arrives at the location indicated by cartridge holder 153*a* in FIG. 19(*a*). The released biochip well is then collected by the robotic arm 158*a* and transported to a test location for further processing.

Of course, many other configurations of the support and drive mechanism are possible. For instance, the drive mechanism 155 and transport module 158 may each be arranged to co-operate with the same cartridge holding position such that no rotation is required between releasing the biochip well and collecting it from the support. The drive mechanism could also be located inside the barrel 151 rather than on the exterior, in which case the cartridges could be loaded in an opposite orientation, or the drive mechanism could be designed to engage the vessel(s) rather than the sealing strip. The barrel design would of course need to provide access through the cartridge holders for the drive mechanism to engage each cartridge.

The relative motion of the support 151 and/or drive mechanism 155 is controlled by a controller 159 which may form part of an analyzer in which the apparatus is incorporated. The controller may include a memory containing information as to the type of biochip carried by each sealed well assembly and programs for controlling the movement of the support and/or drive mechanism to select the appropriate sealed well assembly for dispensation. The controller 159 also controls the dispensing operation through control of the drive mechanism 155 in the same manner as previously described.

FIGS. 19(*b*) to (*f*) show views of an implementation of the same apparatus, in which further details are visible. In these Figures, only selected cartridges holders 153 are labelled, for clarity, and each cartridge holder is empty (i.e. no cartridges are loaded). One well 2 is shown in a released position.

Each cartridge holder 153 comprises an elongate body affixed at either end to the barrel 151. The elongate body includes two side walls 154*a*, 154*b*, parallel and spaced from one another to define a chamber 153*a* therebetween for receipt of a cartridge assembly in use. Once loaded, the cartridge does not extend the full length of the walls 154*a,b*, leaving a region 153*b* ahead of the cartridge empty. This acts as a collection location for the biochip well when it is released from the cartridge.

Upon actuation the cartridge releases a well into the region 153*b*, the impetus imparted to the well by the release action causing the well to be propelled forward. The interior sides of the walls 154*a* and 154*b* are adapted to catch the well and prevent it moving beyond the region 153*b* of its own motion. This is achieved by providing a guide channel at the base of each well 154 which slidably engages the boss 4 provide on the exterior of the well vessel (see FIG. 1), thereby applying a frictional force which slows the motion of the vessel as well as preventing it falling out (e.g. whilst the relevant cartridge holder is upside down). Additionally, a bevelled protruding edge 154*a*' is provided to abut button protrusions 4*a* provided on the exterior of the vessel side walls (see FIG. 1), and to obstruct their passage. The released well is thus retained in the region 153 until it is collected by robotic arm 158*a*. The robotic arm 158*a* grabs the vessel and applies a pulling force which is sufficient to overcome the above described retention features. The robotic arm is then retracted away from the barrel 151 and the well containing the biochip is transported to a test location. The process is repeated for delivery of the next biochip, after rotation of the barrel to present a different cartridge to the drive mechanism if necessary. Any combination of the above described embodiments is also envisaged.

In general terms, the system can therefore comprise of a means to environmentally seal a vessel, mechanically joining a plurality of these vessels using the sealing medium and using this medium to mechanically transport the vessels, where at some stage the path of the foil diverges from the constrained path of the vessel, having the effect of breaking the seal and releasing the vessel.

The invention claimed is:

1. A cartridge configured for a sealed well assembly for the storage of biochips, wherein:
    the sealed well assembly comprises a plurality of vessels affixed to a sealing sheet and arranged along a rectilinear line on the sealing sheet each vessel having at least one well containing a biochip, the well being sealed by the sealing sheet; and the cartridge is configured to accommodate the vessels and comprises a guide structure adapted to constrain movement of the vessels within the cartridge along a vessel path, and to receive the sealing sheet and define a sheet path along which the sealing sheet can travel, the guide structure comprising a guide plate and two side walls defining a cross-section of the guide structure, the vessels of the sealed well assembly being accommodatable therewithin, the guide structure further comprising a plurality of protrusions that form an elongate guide channel, the elongate guide channel defining a vessel path along which movement of the vessels within the guide structure is adapted to be constrained, and the guide plate defining a sealing sheet path along which the sealing sheet can travel, wherein a first section of the vessel path and of the sealing sheet path are parallel and, at a position downstream of the first section, the vessel path and the sealing sheet path diverge such that, in the first section, when the sheet and/or vessels is/are driven, the vessels and sheet remain affixed to one another and, at the diverging position, the sheet is stripped off a respective vessel when the respective vessel reaches the diverging position, thereby opening the well of the respective vessel.

2. The cartridge according to claim 1, further comprising a drive member for transferring drive to the sealed well assembly, and/or a portion of the elongate guide channel is adjacent an end of the cartridge, the elongate guide channel being adapted to cooperate with each vessel so as to prevent rotation thereof or a portion of the elongate guide channel is adjacent an end of the cartridge, the elongate guide channel being adapted to cooperate with each vessel so as to prevent rotation thereof and the elongate guide channel comprises an elongate keying feature adapted to slidably engage with a corresponding feature provided on each vessel.

3. A cartridge assembly comprising the cartridge according to claim 1 and the sealed well assembly.

4. The cartridge assembly according to claim 3, wherein:
a region of the sealing sheet to which the vessels are attached is placed against the guide plate in use; and
the sealing sheet extends around the guide plate so as to form a closed loop, or
a region of the sealing sheet to which the vessels are attached is placed against the guide plate in use; and
the sealing sheet extends around the guide plate so as to form a closed loop and the two ends of the sealing sheet are joined.

5. An apparatus configured to open a sealed well assembly that comprises a plurality of vessels affixed to a sealing sheet and arranged along a rectilinear line on the sealing sheet such that each vessel has at least one well containing a biochip and the well is sealed by the sealing sheet, the apparatus comprising a drive mechanism adapted to convey the sealed well assembly such that the sealing sheet travels along a sheet path and the vessels follow a vessel path, wherein the sheet path and vessel path diverge from one another such that each respective vessel is released from the sealing sheet when the respective vessel reaches the diverging position and the well of the respective vessel is opened.

6. The apparatus according to claim 5 adapted to receive a cartridge comprising a guide structure, wherein the guide structure of the cartridge defines the vessel path and the sheet path, at least in part, and/or the apparatus further comprising a plurality of cartridges that each include a guide structure adapted to constrain movement of the vessels within the cartridge, wherein the guide structure of each cartridge defines a vessel path and a sheet path, at least in part.

7. The apparatus according to claim 5, further comprising a cartridge support structure adapted to receive a plurality of cartridges that each comprise a guide structure, wherein the guide structure of each cartridge defines a respective vessel path and a respective sheet path, at least in part or further comprising a cartridge support structure adapted to receive a plurality of cartridges that each comprise a guide structure, wherein the guide structure of each cartridge defines a respective vessel path and a respective sheet path, at least in part and the drive mechanism is movable relative to the cartridge support structure such that in use the drive mechanism conveys the sealed well assembly in a selected one of the plurality of cartridges carried by the cartridge support structure or further comprising a cartridge support structure adapted to receive a plurality of cartridges that each comprise a guide structure, wherein the guide structure of each cartridge defines a respective vessel path and a respective sheet path, at least in part and a corresponding plurality of drive mechanisms are provided for conveying a plurality of the sealed well assemblies in the plurality of cartridges carried by the cartridge support structure in use.

8. A method of opening a sealed well in a vessel, comprising:
(a) providing the cartridge assembly according to claim 3; and
(b) driving the sealed well assembly such that the sealing sheet follows the sealing sheet path and the vessels follow the vessel path;
wherein the sealing sheet path and vessel path diverge from one another such that each respective vessel is released from the sealing sheet when the respective vessel reaches the diverging position and the well of the respective vessel is opened.

9. The method according to claim 8, wherein the sealing sheet path follows a closed loop or an open path, and/or the vessel path is substantially rectilinear, and/or the vessel path and sheet path are parallel to each other at least in a first region upstream of the point of divergence, and/or in step (a), a plurality of the sealed well assemblies are provided, and the method further comprises, prior to step (b):
(a1) selecting one of the plurality of sealed well assemblies in which a vessel is to be opened; and
(a2) selecting a drive mechanism corresponding to the selected sealed well assembly; or
(a3) moving the plurality of sealed well assemblies relative to a drive mechanism, and/or the method is performed using an apparatus that comprises a drive mechanism adapted to convey the sealed well assembly, or the vessel path and sheet path are parallel to each other at least in a first region upstream of the point of divergence the vessel path and sheet path being rectilinear in the first region.

10. The cartridge assembly according to claim 3, wherein the sealing sheet comprises a metal foil, polymer layer, cellulose-based material, or any combination thereof.

11. The cartridge assembly according to claim 3, wherein each well is a biochip well such that:
each vessel forms at least base and side walls of the respective well and defines at least one aperture giving access to the respective well;
a retaining structure holds the biochip at a predetermined position within the well; and the respective well includes a laterally offset region into which the biochip does not protrude.

12. The cartridge assembly according to claim 11, wherein the laterally offset region is offset in the plane defined by the surface of the biochip when held at the predetermined position by the retaining structure.

13. The cartridge assembly according to claim 11, wherein the shape and/or size of the laterally offset region is such that the biochip cannot be accommodated therewithin.

14. The cartridge assembly according to claim 11, wherein the laterally offset region has a width which decreases with increasing distance from the predetermined position in which the biochip is held.

15. The cartridge assembly according to claim 11, wherein the laterally offset region has a cross section in the lateral plane which is triangular, curved, semi-circular or semi-elliptical.

16. The cartridge assembly according to claim 11, wherein the retaining structure comprises one or more interference fit features provided on the side and/or base walls of the well, adapted to grip the biochip in use.

17. The cartridge assembly according to claim 11, wherein the retaining structure comprises at least one protrusion extending from an internal wall of the well, the at least one protrusion being deformable such that in use the at least one protrusion can be mechanically deformed to extend over a portion of the biochip, when the biochip is at the predetermined position or the retaining structure comprises an adhesive, a mechanical clip, an ultrasonically formed protrusion from a side wall, a mechanical puncture through a side wall, a mechanically formed protrusion from a side wall, a snap-in insert or a collar.

18. The cartridge assembly according to claim 3, wherein the vessels are affixed to the sealing sheet by heat sealing, an adhesive or ultra sonic welding.

19. The cartridge assembly according to claim 3, wherein the sealing sheet extends beyond the perimeter of the vessels in at least one direction, or the sealing sheet extends beyond the perimeter of the vessels in at least one direction and an extended region of the sheet is at least as long as the well in the same direction, or the sealing sheet extends beyond the perimeter of the vessels in at least one direction and an extended region of the sheet is at least as long as the well in the same direction and the length of the extended region is at least as long as the portion of the sheet to which the vessels are attached.

* * * * *